United States Patent
Hibner et al.

(10) Patent No.: US 7,769,426 B2
(45) Date of Patent: *Aug. 3, 2010

(54) METHOD FOR USING AN MRI COMPATIBLE BIOPSY DEVICE WITH DETACHABLE PROBE

(75) Inventors: John Anthony Hibner, Mason, OH (US); Lynetta Jean Freeman, Mason, OH (US); Elizabeth Lynn Sebern, Cincinnati, OH (US); Jessica Mary Pyzoha, Cincinnati, OH (US); Terry Darnell McCoy, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1319 days.

This patent is subject to a terminal disclaimer.

(21) Appl. No.: 10/171,556

(22) Filed: Jun. 12, 2002

(65) Prior Publication Data

US 2003/0199754 A1 Oct. 23, 2003

Related U.S. Application Data

(60) Provisional application No. 60/374,807, filed on Apr. 23, 2002.

(51) Int. Cl.
*A61B 5/05* (2006.01)
(52) U.S. Cl. .................. 600/411; 600/417; 600/414; 600/429; 606/130
(58) Field of Classification Search .............. 600/411, 600/417, 429, 562; 606/130
See application file for complete search history.

(56) References Cited

U.S. PATENT DOCUMENTS 5,211,165 A   5/1993   Dumoulin et al.
5,307,808 A   5/1994   Dumoulin et al.
5,318,025 A   6/1994   Dumoulin et al.
5,437,277 A   8/1995   Dumoulin et al.
5,443,066 A   8/1995   Dumoulin et al.
5,445,150 A   8/1995   Dumoulin et al.

(Continued)

FOREIGN PATENT DOCUMENTS

EP   0995400   4/2000
FR   2332743   6/1977
WO   WO 02/13709   2/2002

OTHER PUBLICATIONS

RSNA Nov. 1999, vol. 213, p. 454 (#1521) The MR-Compatible Mammotome.
European Search Report, dated Jan. 5, 2004 for EPO Application No. 03252518.0.
Kuhl, C.K., et al., "Interventional Breast MR Imaging: Clinical Use of a Stereotactic Localization and Biopsy Device," Radiology, vol. 204 (1997) pp. 667-675.

*Primary Examiner*—Brian Casler
*Assistant Examiner*—John F Ramirez

(57) ABSTRACT

A method for performing Magnetic Resonance Imaging (MRI) guided core biopsies is tendered more accurate and efficient by precisely positioning a disengaged probe assembly with respect to a localization fixture attached to a breast coil platform. The precise position is defined by MRI stereotopic location of suspicious tissue with respect to a fiducial marker on the localization fixture. With the probe inserted, dual lumens in the probe assembly are used for drainage or insertion of fluids as well as inserting diagnostic and therapeutic tools. Core biopsies are performed by engaging a biopsy instrument handle containing a cutter, with the localization fixture providing support and position to the handle. Repeated MRI scans are facilitated by the ability to disengage the handle without risk of displacing the probe assembly from the biopsy site.

23 Claims, 21 Drawing Sheets

U.S. PATENT DOCUMENTS

| | | | | |
|---|---|---|---|---|
| 5,526,822 A | | 6/1996 | Burbank et al. | |
| 5,534,778 A | * | 7/1996 | Loos et al. | 324/318 |
| 5,560,373 A | | 10/1996 | De Santis | |
| 5,569,266 A | * | 10/1996 | Siczek | 606/130 |
| 5,649,547 A | | 7/1997 | Ritchart et al. | |
| 5,678,549 A | | 10/1997 | Heywang-Koebrunner | 128/653.5 |
| 5,685,847 A | * | 11/1997 | Barry | 604/96.01 |
| 5,715,822 A | | 2/1998 | Watkins et al. | |
| 5,775,333 A | | 7/1998 | Burbank et al. | 128/754 |
| 5,830,219 A | | 11/1998 | Bird et al. | 606/130 |
| 5,855,554 A | | 1/1999 | Schneider et al. | 600/407 |
| 5,882,305 A | | 3/1999 | Dumoulin et al. | |
| 5,913,863 A | | 6/1999 | Fischer et al. | 606/130 |
| 6,021,342 A | | 2/2000 | Brabrand | |
| 6,022,325 A | | 2/2000 | Siczek et al. | 600/568 |
| 6,036,632 A | | 3/2000 | Whitmore, III et al. | 600/7 |
| 6,077,230 A | | 6/2000 | Gregoire et al. | 600/566 |
| 6,086,544 A | | 7/2000 | Hibner et al. | |
| 6,142,955 A | | 11/2000 | Farascioni et al. | 600/562 |
| 6,161,034 A | * | 12/2000 | Burbank et al. | 600/431 |
| 6,174,291 B1 | | 1/2001 | McMahon et al. | 600/166 |
| 6,261,241 B1 | | 7/2001 | Burbank et al. | 600/564 |
| 6,270,506 B1 | | 8/2001 | Sittek et al. | 606/130 |
| 6,287,304 B1 | * | 9/2001 | Eggers et al. | 606/37 |
| 6,289,233 B1 | | 9/2001 | Dumoulin et al. | |
| 6,590,417 B1 | | 7/2003 | Jones et al. | |
| 6,638,235 B2 | * | 10/2003 | Miller et al. | 600/566 |
| 6,685,666 B1 | * | 2/2004 | Fontenot | 604/27 |
| 6,846,320 B2 | | 1/2005 | Ashby et al. | |
| 6,889,073 B2 | | 5/2005 | Lampman et al. | |
| 7,192,404 B2 | | 3/2007 | Rhad et al. | |
| 2001/0039378 A1 | | 11/2001 | Lampman et al. | |
| 2002/0156365 A1 | | 10/2002 | Tsekos | |
| 2003/0083592 A1 | * | 5/2003 | Faciszewski | 600/564 |
| 2003/0199753 A1 | | 10/2003 | Hibner et al. | |
| 2003/0199785 A1 | | 10/2003 | Hibner et al. | |

* cited by examiner

METHOD FOR USING AN MRI COMPATIBLE BIOPSY DEVICE WITH DETACHABLE PROBE

CROSS REFERENCE TO RELATED APPLICATIONS

The present application hereby claims the benefit of the provisional patent application of the same title, Ser. No. 60/374,807 filed on Apr. 23, 2002. The present application is related to co-pending and commonly-owned applications filed on even date herewith entitled "LOCALIZATION MECHANISM FOR AN MRI COMPATIBLE BIOPSY DEVICE" to Hibner et al. and "AN MRI COMPATIBLE BIOPSY DEVICE WITH DETACHABLE PROBE" to Hibner et al., the disclosure of both is hereby incorporated by reference in their entirety.

FIELD OF THE INVENTION

The present invention relates, in general to a method of imaging assisted tissue sampling and, more particularly, to an improved method for positioning a biopsy probe with respect to a magnetic resonance imaging (MRI) breast coil for acquiring subcutaneous biopsies and for removing lesions.

BACKGROUND OF THE INVENTION

The diagnosis and treatment of patients with cancerous tumors, pre-malignant conditions, and other disorders has long been an area of intense investigation. Non-invasive methods for examining tissue are palpation, Thermography, PET, SPECT, Nuclear imaging, X-ray, MRI, CT. and ultrasound imaging. When the physician suspects that tissue may contain cancerous cells, a biopsy may be done either in an open procedure or in a percutaneous procedure. For an open procedure, a scalpel is used by the surgeon to create a large incision in the tissue in order to provide direct viewing and access to the tissue mass of interest. Removal of the entire mass (excisional biopsy) or a part of the mass (incisional biopsy) is done. For a percutaneous biopsy, a needle-like instrument is used through a very small incision to access the tissue mass of interest and to obtain a tissue sample for a later examination and analysis. The advantages of the percutaneous method as compared to the open method are significant: less recovery time for the patient, less pain, less surgical time, lower cost, less risk of injury to adjacent bodily tissues such as nerves, and less disfigurement of the patient's anatomy. Use of the percutaneous method in combination with artificial imaging devices such as X-ray and ultrasound has resulted in highly reliable diagnoses and treatments.

Generally there are two ways to percutaneously obtain a portion of tissue from within the body, by aspiration or by core sampling. Aspiration of the tissue through a fine needle requires the tissue to be fragmented into small enough pieces to be withdrawn in a fluid medium. The method is less intrusive than other known sampling techniques, but one can only examine cells in the liquid (cytology) and not the cells and structure (pathology). In core sampling, a core or fragment of tissue is obtained for histologic examination, genetic tests, which may be done via a frozen or paraffin section. The type of biopsy used depends mainly on various factors present in the patient, and no single procedure is ideal for all cases. However, core biopsies seem to be more widely used by physicians.

Recently, core biopsy devices have been combined with imaging technology to better target the lesion. A number of these devices have been commercialized. One such commercially available product is marketed under the trademark name MAMMOTOME™, Ethicon Endo-Surgery, Inc. An embodiment of such a device is described in U.S. Pat. No. 5,526,822 issued to Burbank, et al., on Jun. 18, 1996, and is hereby incorporated herein by reference.

As seen from that reference, the instrument is a type of image-guided, percutaneous, coring, breast biopsy instrument. It is vacuum-assisted, and some of the steps for retrieving the tissue samples have been automated. The physician uses this device to capture "actively" (using the vacuum) the tissue prior to severing it from the body. This allows the sampling of tissues of varying hardness. The device can also be used to collect multiple samples in numerous positions about its longitudinal axis, and without removing the device from the body. These features allow for substantial sampling of large lesions and complete removal of small ones.

Co-pending application Ser. No. 09/825,899 filed on Apr. 2, 1997, which is hereby incorporated herein by reference, described other features and potential improvements to the device including a molded tissue cassette housing permitting the handling and viewing of multiple tissue samples without physical contact by the instrument operator. Another described therein is the interconnection of the housing to the piercing needle using a thumbwheel, to permit the needle to rotate relative to the housing, while preventing the vacuum tube from wrapping about the housing. During use, the thumbwheel is rotated so that the device rotates within the lesion, and samples can be taken at different points within the lesion.

In actual clinical use for breast biopsy the instrument (probe and driver assembly) is mounted to the three axis-positioning head of an x-ray imaging machine. The three axis-positioning head is located in the area between the x-ray source and the image plate. The x-ray machines are outfitted with a computerized system which requires two x-ray images of the breast be taken with the x-ray source at two different positions in order for the computer to calculate x, y and z axis location of the suspect abnormality. In order to take the stereo x-ray images the x-ray source must be conveniently movable. The x-ray source therefore is typically mounted to an arm which, at the end opposite the x-ray source, is pivotally mounted to the frame of the machine in the region of the image plate.

Recently, there has been a need for a hand held core sampling biopsy device. This need has been fulfilled by Ethicon-Endo Surgery in U.S. Pat. No. 6,086,544 issued on Jul. 11, 2000, which is hereby incorporated herein by reference. This aforementioned patent discloses a hand-held MAMMO-TOME™ that may be held approximately parallel to the chest wall of the patient for obtaining tissue portions close to the chest wall and may be manipulated by the operator's hand. Thus, the operator may steer the tip of the handpiece on the MAMMOTOME™ with great freedom towards the tissue mass of interest. The surgeon has tactile feedback while doing so and can thus ascertains to a significant degree, the density and hardness of the tissue being encountered. In addition, a hand-held MAMMOTOME™ is desirable because the handpiece on the MAMMOTOME™ may be held approximately parallel to the chest wall of the patient for obtaining tissue portions closer to the chest wall than may be obtained when using an instrument that is mounted to an electromechanical arm.

Recently, there has been a desire to use the above described biopsy devices with MRI imaging devices instead of x-ray imaging devices. However, existing medical biopsy sampling devices use small, multi-lumen probes extensively fabricated mostly if not entirely from metal. However, the ability to provide accurate minimally invasive diagnosis of suspicious breast lesions hinges on the size of the sample obtained and accuracy in placement of the sampling device.

The metallic nature of these probes has many drawbacks. Typically these metal probes are electrically conductive and often magnetically weak, which interferes with their use under MRI guidance. The electrically conductive and magnetically weak nature of metal probes often work to create field distortions, called artifacts, on the image. The image of the lesion will show the metal probe, and this is problematic because the image of the probe can obscure the image of the lesion.

The small sample size of conventional biopsy needles also presents a significant limitation due to the increase in the duration of the procedure. Due to the tendency for contrast agent to "wash out" of suspicious lesions, and the progressive increase in enhancement of surrounding non-malignant breast parenchyma, suspicious lesions may become indistinguishable to the breast parenchyma within a few minutes. This limits the number of samples that can be retrieved using conventional spring-loaded core biopsy needles under direct imaging guidance.

A further problem not infrequently encountered during core needle biopsy is the development of a hematoma at the biopsy site during the procedure. An accumulating hematoma can be problematic during MRI-guided biopsy because residual contrast agent circulating in the hematoma can mimic enhancement in a suspicious lesion. In addition, the accumulation of air at the biopsy site can cause susceptibility artifacts that can potentially interfere with the fat-suppression MRI techniques at the biopsy site cavity.

These limitations of conventional biopsy needles have led several authors to conclude that lesions should be at least 1 cm in diameter before imaging could confirm that the MRI-guided biopsy device was definitely within (as opposed to adjacent to) the suspicious target. However, the demand for minimally invasive MRI-guided core biopsy is greatest for small lesions because they are more common, more difficult to characterize on MRI grounds alone, and have the best prognosis if they are found to be malignant.

Therefore, there has been a desire to have generally non-metallic (especially non-ferromagnetic) biopsy probe of the type described above to eliminate artifacts. These needs have been filled by co-pending and commonly-owned application Ser. No. 10/021,680, "AN MRI COMPATIBLE SURGICAL BIOPSY DEVICE" to Huitema et al filed on Dec. 12, 2001, the disclosure of which is hereby incorporated by reference in its entirety. The lack of undesirable artifacts for the disclosed hand-held biopsy device allows the accurate placement of the probe. Moreover, disclosed vacuum assist allows visualization of the lesion entering a bowl of the probe to confirm accurate placement, as well as avoiding problems associated with a hematoma or an air cavity. Moreover, the volume and ability to rapidly rotate the open cutting bowl of the probe allows for multiple samples in succession without removal of the probe. Thereby, the duration of the procedure is reduced.

However, elimination of the artifact created by the metal probe entirely is also problematic because physicians rely extensively on some type of artifact to notify them as to where the tip of the probe is relative to the lesion. These needs have been filled by co-pending and commonly-owned application Ser. No. 10/021,407, entitled "AN MRI COMPATIBLE BIOPSY DEVICE HAVING A TIP WHICH LEAVES AN ARTIFACT" to Rhad et al., filed on Dec. 12, 2001, the disclosure of which is hereby incorporated by reference in their entirety. Having a target in the cutter at the distal end of the probe helps avoid advancing the probe through the chest cavity as well as accurately placing the bowl of the probe adjacent to the suspicious tissue for drawing into the cutting bowl.

While the aforementioned hand-held MRI compatible biopsy devices provide many advantages, opportunities exist for improvements and additional clinical functionality. For instance, the hand-held biopsy device presents a long, external handle that is inappropriate for closed magnet MRI machines. Furthermore, while the hand-held biopsy device allows great freedom in lateral and angular orientation, in some instances it is preferable to specifically position the biopsy probe. The MRI machine may provide very accurate stereotactic placement information that is only partially utilized in inserting the probe. In particular, the hand-held biopsy device is inserted through an opening in a compression plate, so some two-dimensional alignment is provided. However, the angle and depth of insertion the probe tends to vary, especially without continual reimaging of the probe during insertion, which is particularly inappropriate for closed MRI magnets.

Furthermore, the vacuum assist reduces occurrence of a hematoma and draws in tissue to increase the sample size without repositioning the probe; however, current clinical procedures often require additional invasive procedures to the biopsy site to administer anesthesia or to perform additional diagnostic or treatment procedures.

Consequently, a significant need exists for a method of performing MRI-guided biopsy that is applicable to both open and closed MRI machines, especially a method that allows a range of diagnostic and therapeutic operations at the biopsy site with a minimum of invasive procedures.

BRIEF SUMMARY OF THE INVENTION

The invention overcomes the above-noted and other deficiencies of the prior art by providing a method whereby a core biopsy is accurately and efficiently performed even with only intermittent Magnetic Resonance Imaging (MRI) scans. The stereotopically derived coordinates of the suspicious tissue are used by a surgeon to position alignment positioning guides on a localization mechanism that guide a core biopsy tool. Thereby, even closed MRI machines may be used since constant monitoring of the position of the core biopsy tool during insertion by MRI guidance is not required.

In one aspect of the invention, a method of MRI guided core biopsy of suspicious breast tissue of a patient's breast includes localizing the patient's breast in the localization fixture, attaching a probe assembly to the probe assembly guide, positioning the probe assembly guide for a desired spatial coordinate, inserting the probe assembly using the probe assembly guide to a desired biopsy site, and engaging a biopsy instrument handle to the probe assembly. The biopsy instrument handle includes a cutter that translates within the probe assembly to perform the core biopsy.

In another aspect of the invention, a method of MRI guided core biopsy of suspicious breast tissue is enhanced with a fiducial marker that is coupled to the localization mechanism. Thereby, stereotopic coordinates for suspicious tissue are readily and accurately made with respect to the localization mechanism. Since the localization mechanism also positions and guides the core biopsy tool, increased accuracy is achievable.

In yet another aspect of the invention, a method of diagnostic imaging guided biopsy includes positioning a probe at a specified spatial coordinate on a compression plate of a localization fixture, thereby accurately specifying the insertion point for the probe. Thereafter constraining movement of the probe along an insertion angle for a specified distance to the desired biopsy location. Maintaining the insertion angle avoids the need to active image the probe during insertion to avoid an error due to the angle of insertion of under or over travel during insertion.

These and other objects and advantages of the present invention shall be made apparent from the accompanying drawings and the description thereof.

DETAILED DESCRIPTION OF THE INVENTION

Figure 1:
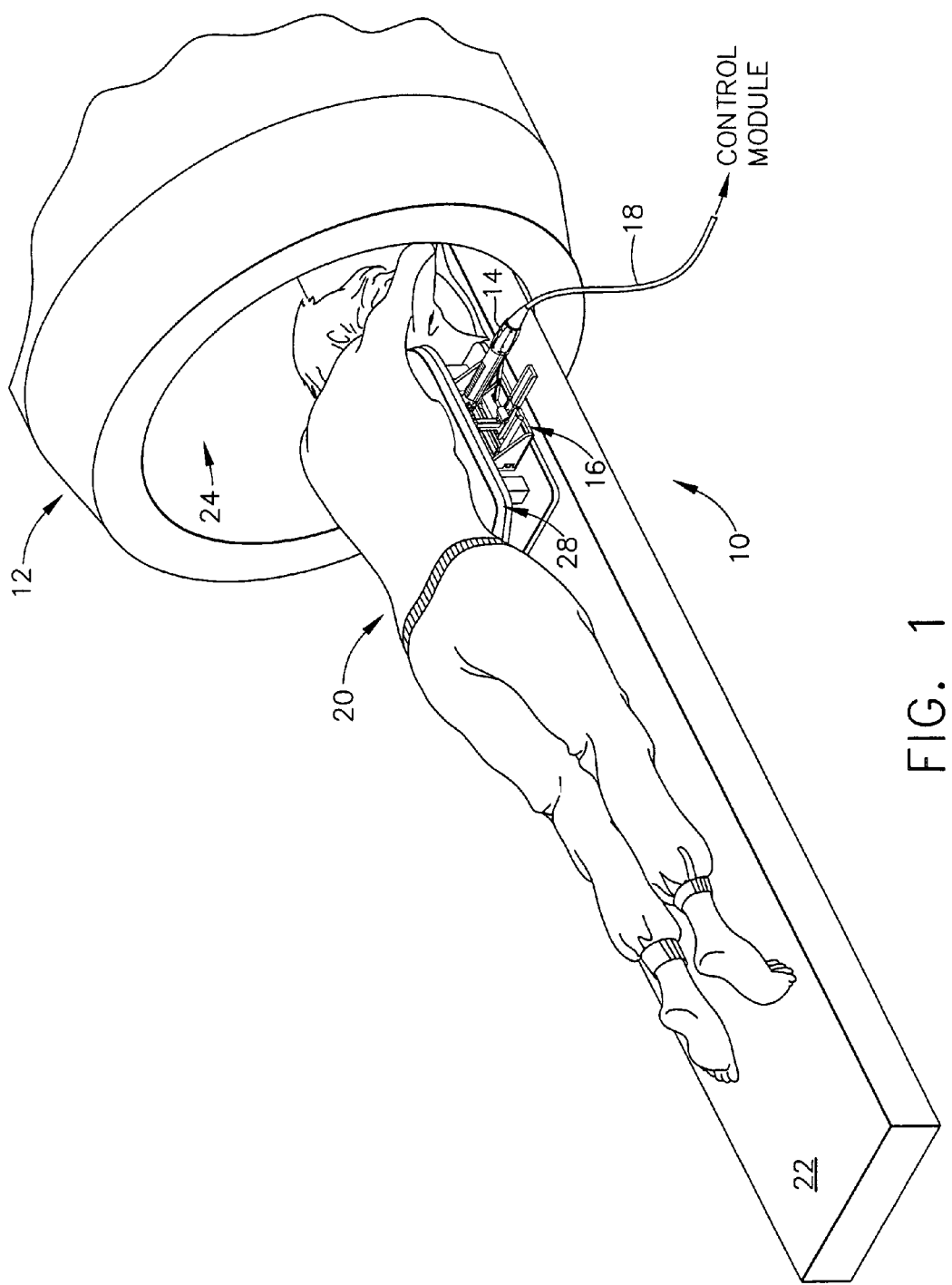
FIG. 1 is plan view of the biopsy instrument, mounting fixture, an Magnetic Resonance Imaging (MRI) breast coil fixture, and patient support table in working relationship outside the confines of an MRI machine.

FIG. 1 depicts a core biopsy instrument system 10 that is vacuum assisted, detachable, and compatible with use in a Magnetic Resonance Imaging (MRI) machine, such as the depicted closed MRI machine 12. In the illustrative embodiment, the core biopsy instrument system 10 includes an MRI-compatible biopsy tool 14 that is selectably attached to a localization mechanism or fixture 16 to accurately and rapidly perform core biopsies of breast tissue with a minimum of insertions of a biopsy probe. A control module (not shown) senses encoder position signal and switch signals from the biopsy tool 14 and provides mechanical and vacuum power to the biopsy tool 14 via power cord 18.

Figure 2:
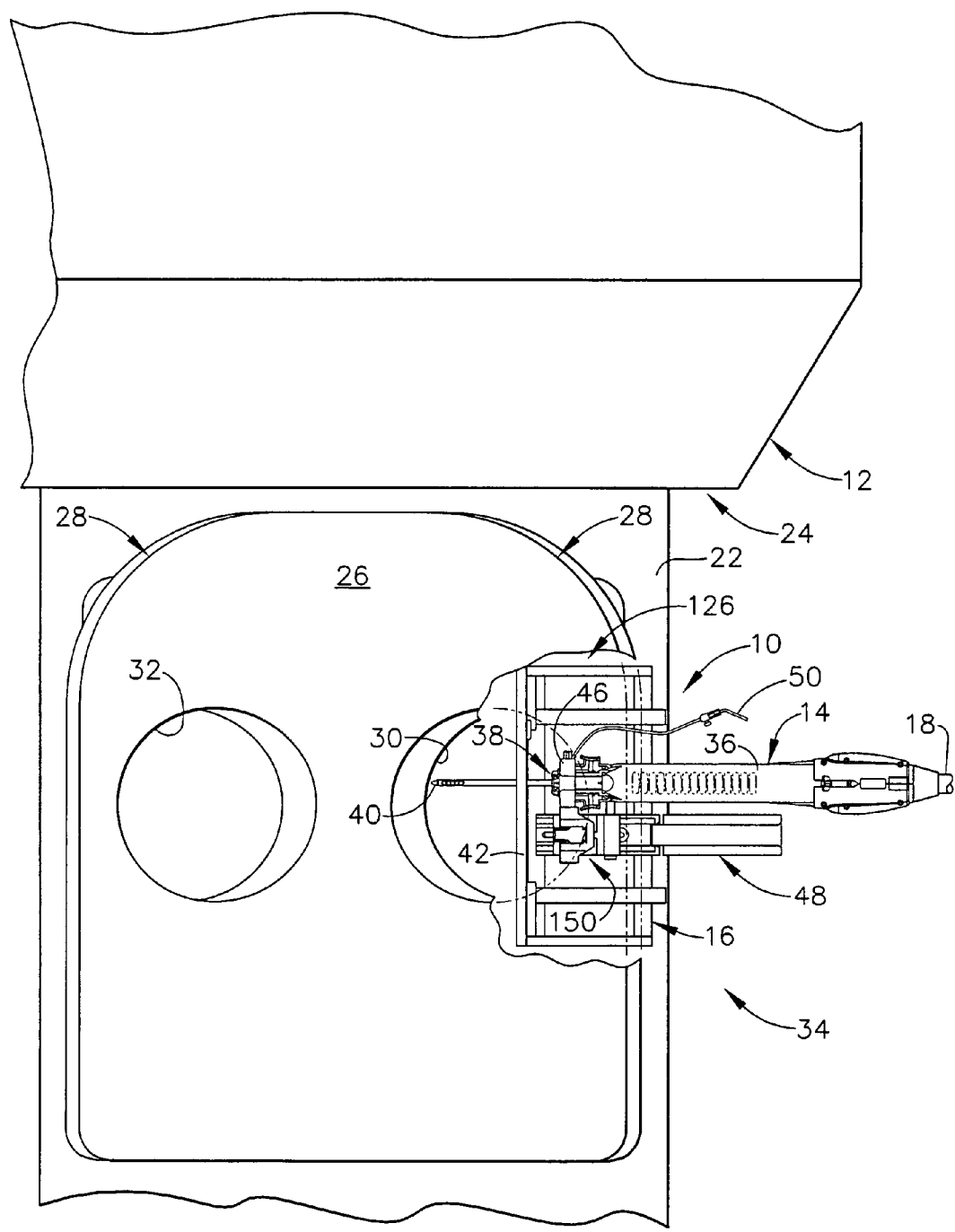
FIG. 2 is a plan view of the biopsy instrument, localization fixture, partially cut away MRI breast coil fixture, patient support table, and in working relationship and configured for insertion into a MRI machine.

With reference to FIGS. 1-2, a patient 20 is lying prone upon a patient support table 22, depicted in FIG. 1 as removed from a magnet bore 24 of the MRI machine 12. The patient's chest rests upon a top surface 26 of a chest support 28, the top surface 26 having openings 30, 32 for allowing the patient's breasts to hang downward for imaging and treatment. With particular reference to FIG. 2, the right opening 30 is depicted with the localizer fixture 16 laterally positioned to cooperate with a medial compression plate (not shown) to longitudinally fix and compress the patient's right breast. Antenna elements (not shown) are placed about the opening 30 to detect radio frequency (RF) signals emanated from breast tissue induced by a strong magnetic field from the MRI bore 24. The chest support 28, localization fixture 16, and antennas are, collectively, generally termed a breast coil 34.

The biopsy tool 14 includes a biopsy handle 36 that is attachable to a probe assembly 38. The localization fixture 16 accurately positions the probe assembly 38 for stereotactic mammography biopsy procedures for a specific biopsy site location for a distal tip 40 of the probe assembly 38. This location is identified by an X-axis coordinate that is horizontal and longitudinal with respect to the patient (up and down in FIGS. 2 and 3). A Z-axis is defined as the vertical height, with the X and Z axis orthogonally defined on a lateral compression plate 42 of the localization fixture 16, the lateral compression plate 42 cooperating with the medial compression plate (not shown) to fix and compress the patient's breast. This location is also defined in terms of depth of insertion, or Y-axis, which is horizontal and transverse with respect to the patient (right to left in FIGS. 2 and 3). A probe assembly mounting device 150 connects to a probe housing 46 of the biopsy tool 14.

The mounting device 150 includes alignment positioning guides (described in more detail below) to orient the probe housing 46, and hence the probe assembly 38, to the desired X-Y-Z coordinate. For instance, a depth slide 48 allows mounting of the probe assembly 38 with the distal tip 40 extending outside of the opening 30 and lateral compression plate 42. Thereafter, the probe assembly 38 is guided along the Y-axis by the depth slide 48 while maintaining the selected X-Z-axes coordinates. In addition, the mounting device 150 advantageously supports the biopsy handle 36 when attached to the probe assembly 38 as depicted in FIG. 2 to maintain the angle of insertion of the probe assembly 38. The probe housing 46 provides access to the interior of the probe assembly 38 via a vacuum lumen access conduit 50 for draining fluids, inserting fluids such as anesthetics.

Figure 3:
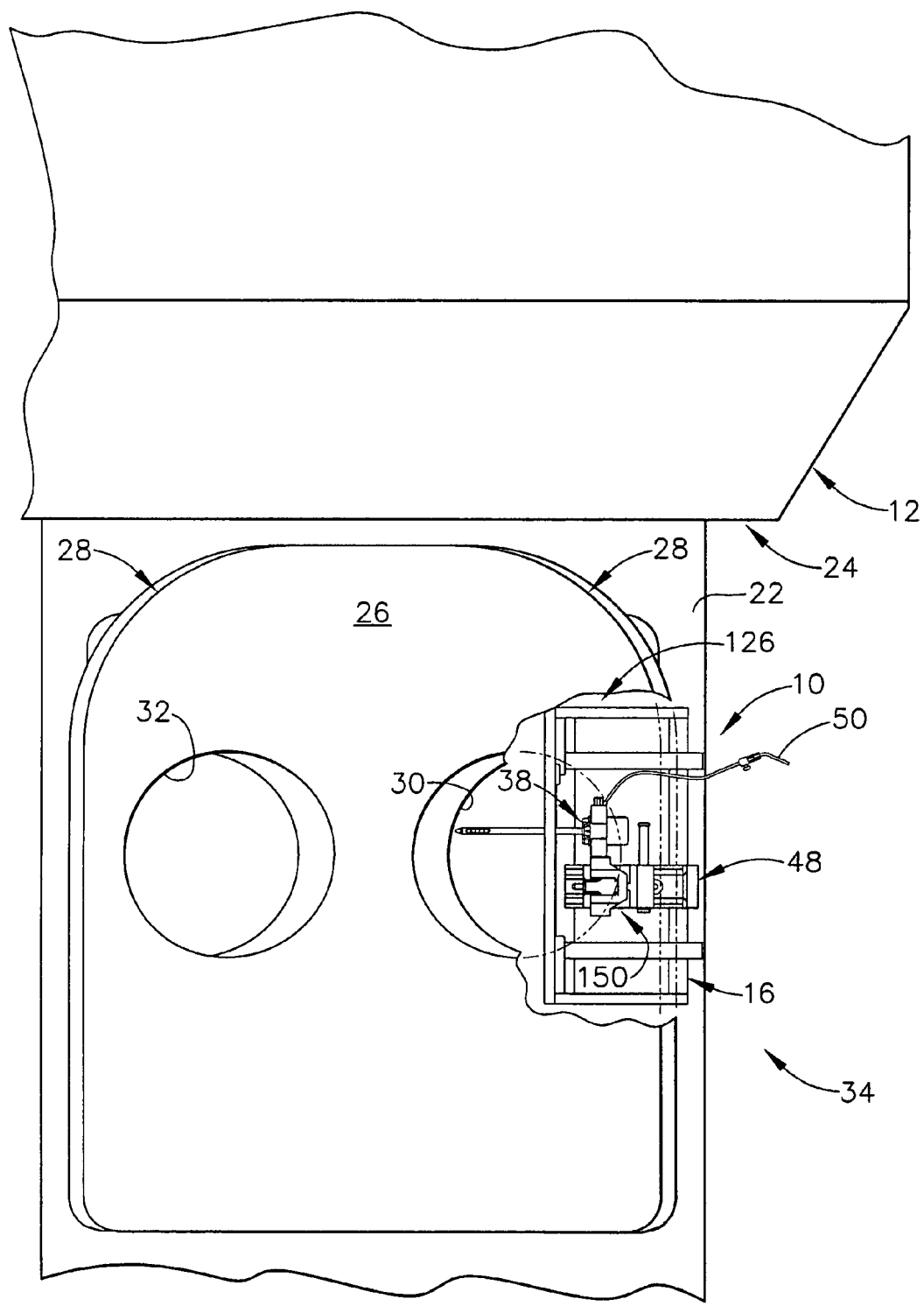
FIG. 3 is a plan view of the localization fixture, partially cut away MRI breast coil fixture, patient support table, and a detached probe assembly of the biopsy instrument mounted to the localization fixture, in working relationship and configured for insertion into the MRI machine.

FIG. 3 depicts the core biopsy instrument system 10 with the biopsy handle 36 removed and the depth slide 48 moved inward to allow insertion of the patient support table 22 into the narrow confines of the MRI magnet bore 24. Moreover, the surgeon may take full advantage of the stereotactic coordinates provided by the MRI machine 12, even if using a closed magnetic bore 24. In particular, the stereotactic derived coordinates may be used even if not actively imaging the probe assembly 38 during insertion. The localization fixture 16 enables the surgeon to manually insert the probe assembly 38 in depth with an indication of current depth. The surgeon is given tactile feedback while doing so and can thus ascertain to a significant degree the density and hardness of tissue being encountered. In addition, with the probe assembly 38 maintained in the correct location after insertion, the probe assembly 38 provides access for other diagnostic and therapeutic tools and fluid treatments.

Alternatively or in addition, a depth adjustment mechanism may be incorporated into the localization fixture 16 to provide mechanical advantage, thereby achieving a controlled and deliberate insertion of the probe assembly 38. Moreover, the depth adjustment mechanism may incorporate a frictional, ratcheting or locking feature to prevent inadvertent movement of the probe assembly 38 after placement at the desired biopsy location. Examples of such depth adjustment include but are not limited to a thumb wheel in geared communication between the probe assembly mounting device 150 and the localizer support frame 126.

Figure 4:
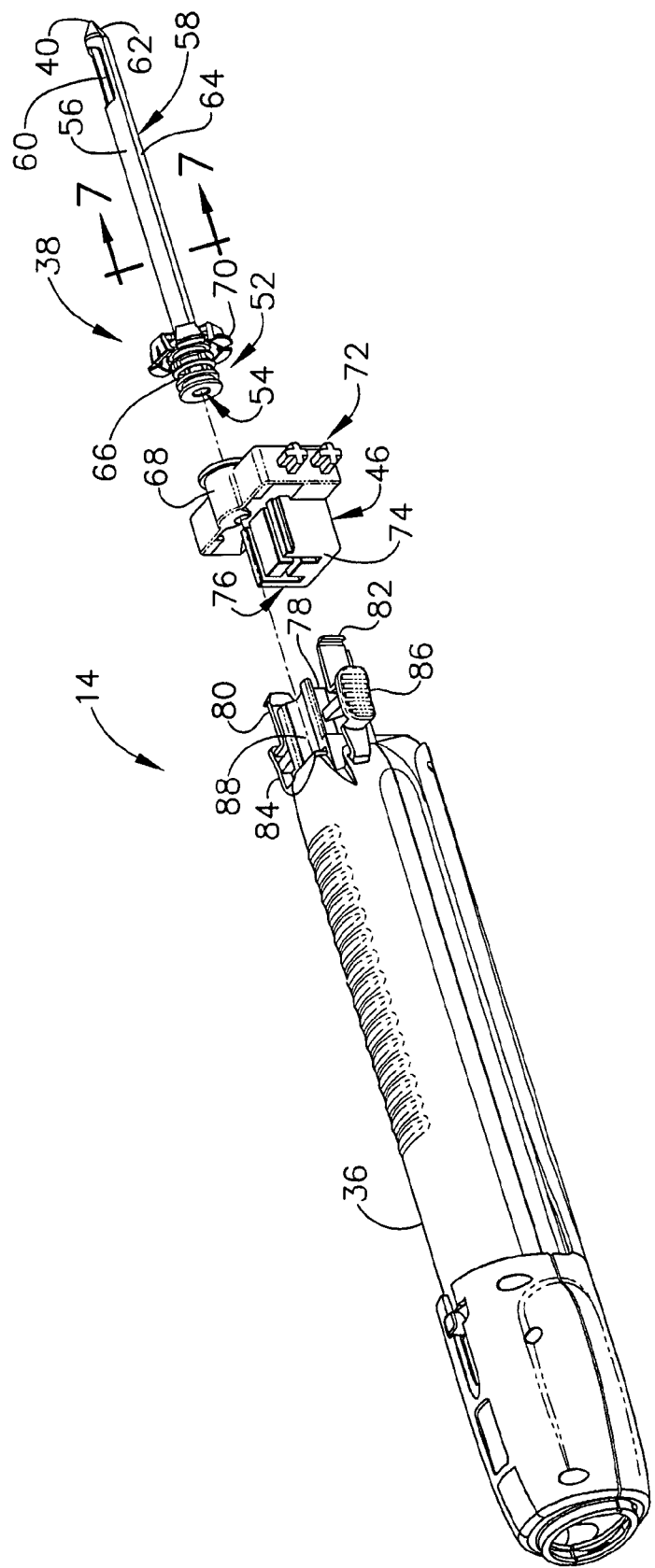
FIG. 4 is an isometric view of the biopsy instrument disassembled into a biopsy instrument handle, probe housing, and probe.
Figure 4A:
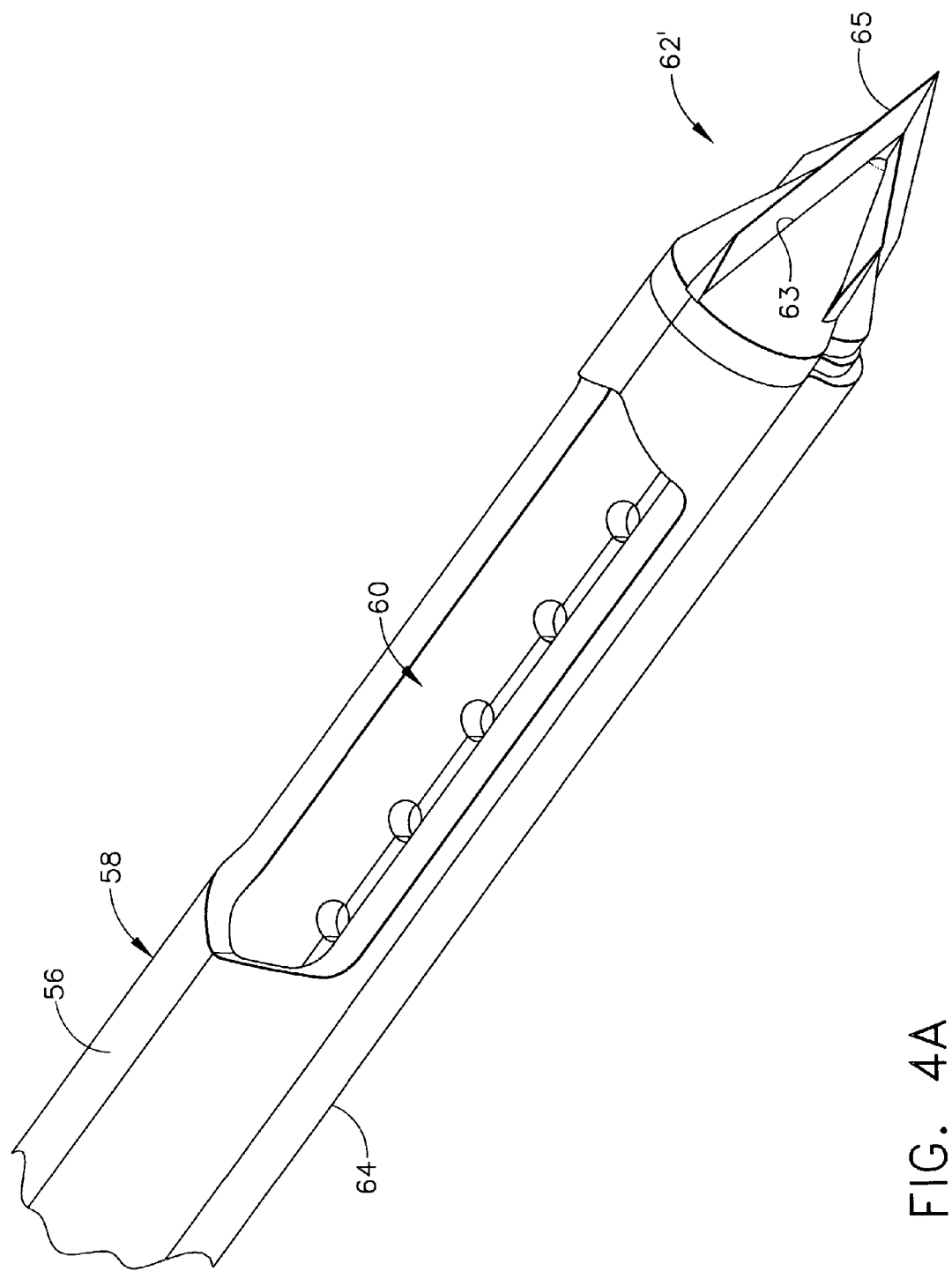
FIG. 4A is a frontal isometric detail view of an alternative needle tip of a biopsy instrument.

FIG. 4 depicts the biopsy tool 14 with the biopsy handle 36 depicted as readily attached to the probe housing 46, which in turn is readily attached to the probe assembly 38. The probe assembly 38 includes a male cylindrical mating portion 52 presenting a central cutter opening 54 on a proximal end that is aligned with the longitudinal length of a cutter lumen 56 of an elongated needle 58. The cutter lumen 56 communicates with a sample port 60 laterally presented near a needle tip 62 at the distal end of the needle 58. The needle tip 62 is for penetrating the soft tissue of a surgical patient. The needle tip 62 is sharpened and is preferably made from an MRI compatible resin such as ULTEM or VECTRA. In the illustrative embodiment, the needle tip 62 is a three-sided pyramidal shaped point, although the needle tip 62 configuration may also have other shapes and/or inserts. In addition, as in the aforementioned application Ser. No. 10/021,407, entitled "AN MRI COMPATIBLE BIOPSY DEVICE HAVING A TIP WHICH LEAVES AN ARTIFACT", the illustrative embodiment advantageously includes a material that leaves a small, but not troublesome artifact on an MRI scan.

Referring back to FIG. 4, it will be appreciated that a cutter element or an obturator stylet is advanced inside the cutter lumen 56 to block the sample port 60 during insertion. Once the needle 58 is positioned, the sample port 60 is exposed to allow tissue to enter. In particular, a vacuum may be presented to a "sample bowl" inside the cutter lumen 56 near the sample port 60 by applying vacuum power through a vacuum chamber lumen 64 that communicates along the longitudinal length of the needle 58 to the male cylindrical mating portion 52. In particular, a series of small holes allow gas and fluid to enter the vacuum chamber lumen 64 from the sample port 60 but prevent tissue samples from entering.

Annular rings 66 about the cylindrical mating portion 52 grip and seal to an interior of a female cylindrical mating portion 68 on the probe housing 46. Between annular rings 66, a proximal vacuum port (not shown in FIG. 4) communicates with a vacuum passage (not shown) in the probe housing 46. The engagement between the mating portions 52, 68 advantageously allows rotation of the needle 58 with a thumb wheel 70 annularly presented near the proximal end of the needle 58. The radial opening presented by the annular rings 66 maintains communication between the vacuum passage in the probe housing 46 and the vacuum chamber lumen 64 regardless of radial orientation of the needle 58. Thereby, the sample port 60 may be presented to tissue at any and all radial positions about the distal end of the needle 58. With the assistance of vacuum, a large volume of tissue may be selectably drawn into the sample bowl for biopsy sampling.

Figure 9:
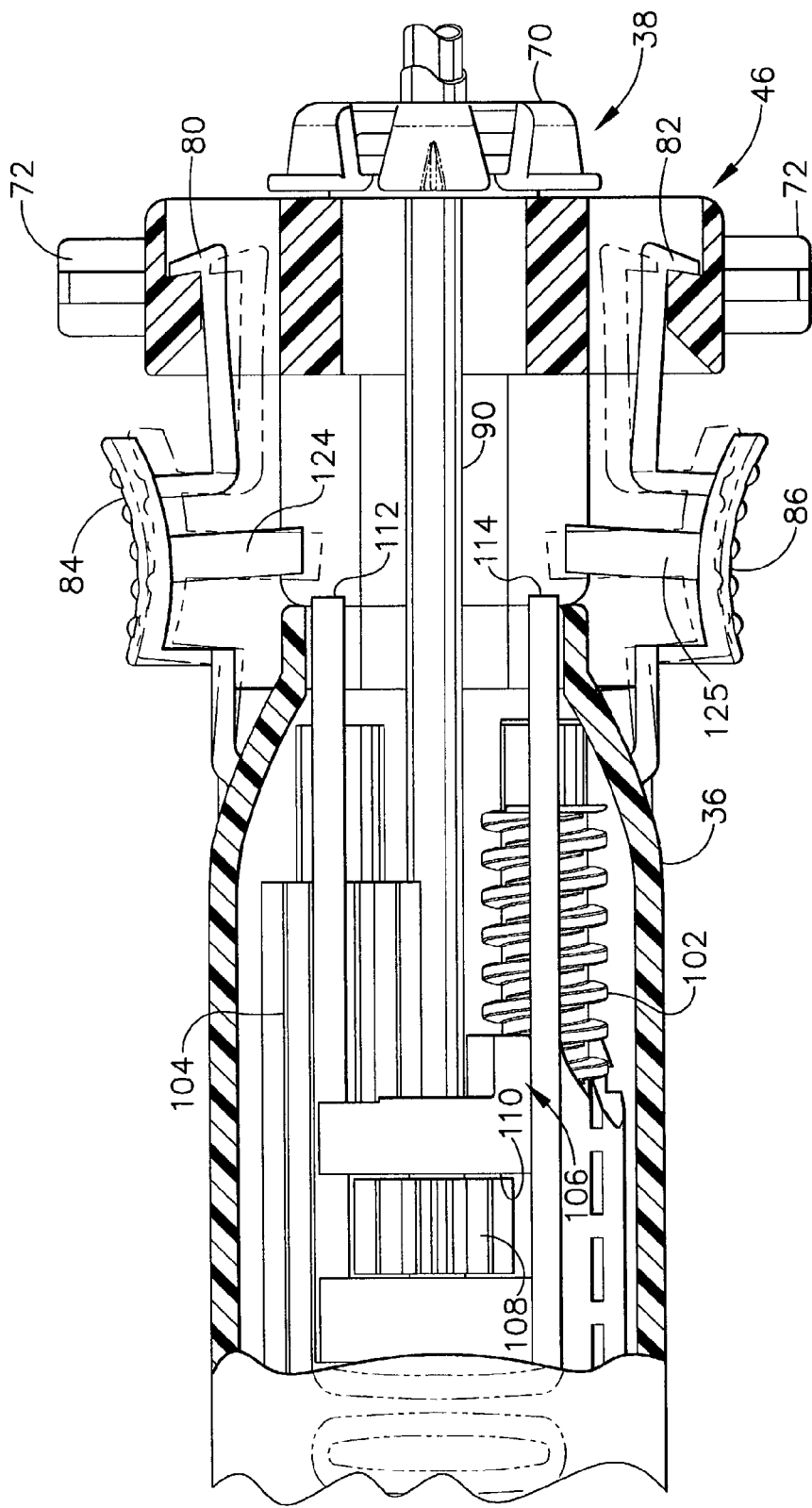
FIG. 9 is a fragmentary plan view in partial section of the distal portion of the handle and probe housing and assembly, illustrating the disconnect feature with the cutter retracted.
Figure 10:
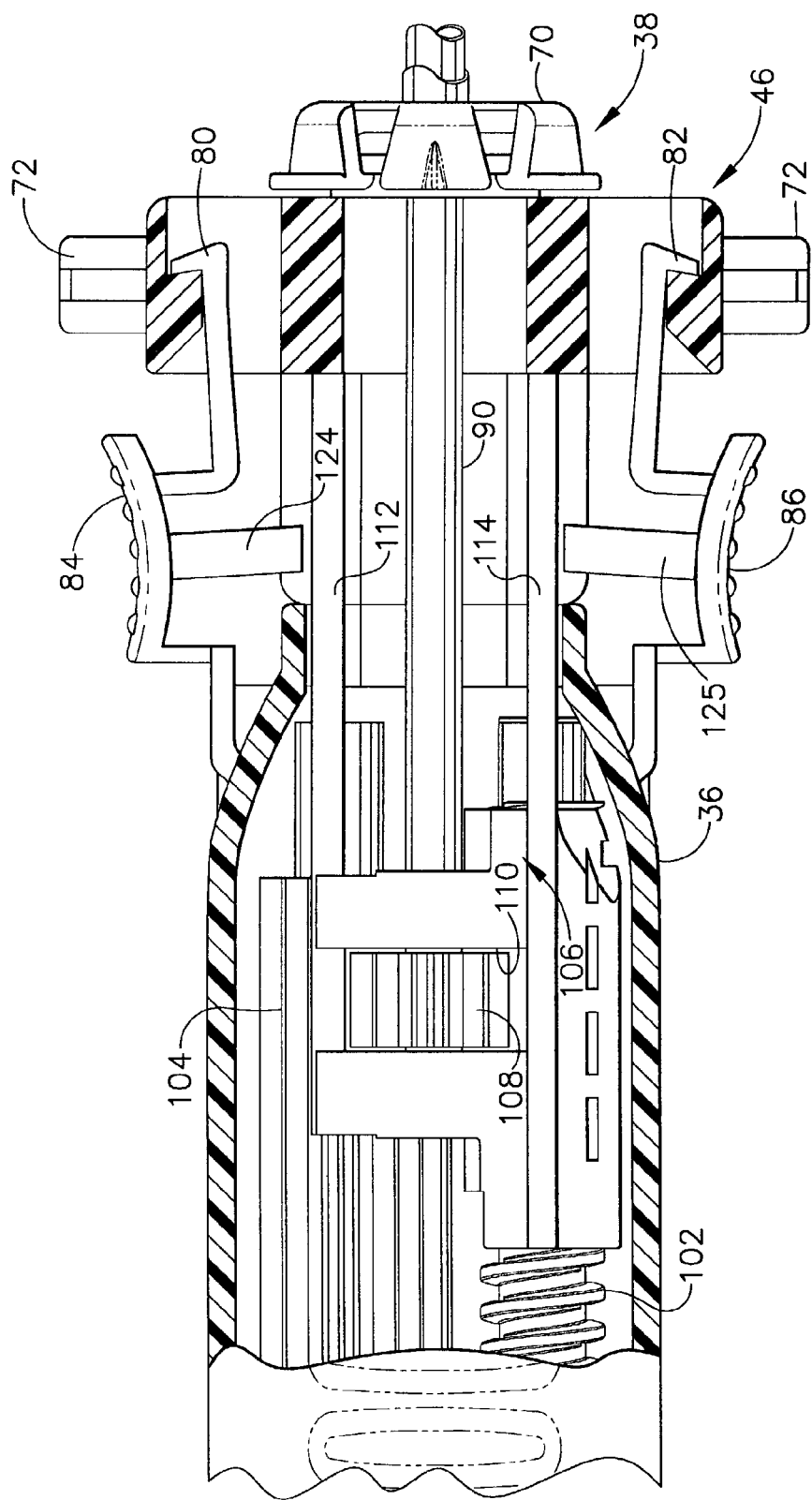
FIG. 10 is a fragmentary plan view in partial section of the distal portion of the handle and probe housing and assembly, illustrating the tolerance take-out feature and the disabled disconnect feature when the cutter is advanced.

The probe housing 46 includes laterally presented attachment prongs 72 for mounting to the localization fixture 16. In addition, the probe housing 46 presents a proximally directed cuboidal engagement member 74 with longitudinally aligned vertical and horizontal grooves 76 for flanges 78 from the biopsy handle 36. Referring to FIGS. 9 and 10, the probe housing 46 also receives hooked locking tabs 80, 82 on the distal engaging end of the biopsy handle 36 for selective locking and unlocking under the influence of a pair of opposing depression grips 84, 86 attached to respective tabs 80, 82. The biopsy handle 36 includes a sample window 88 for extracting any tissue sample withdrawn from the cutter lumen 52 under the influence of a vacuum passing through the cutter, as described in more detail below.

Figure 5:
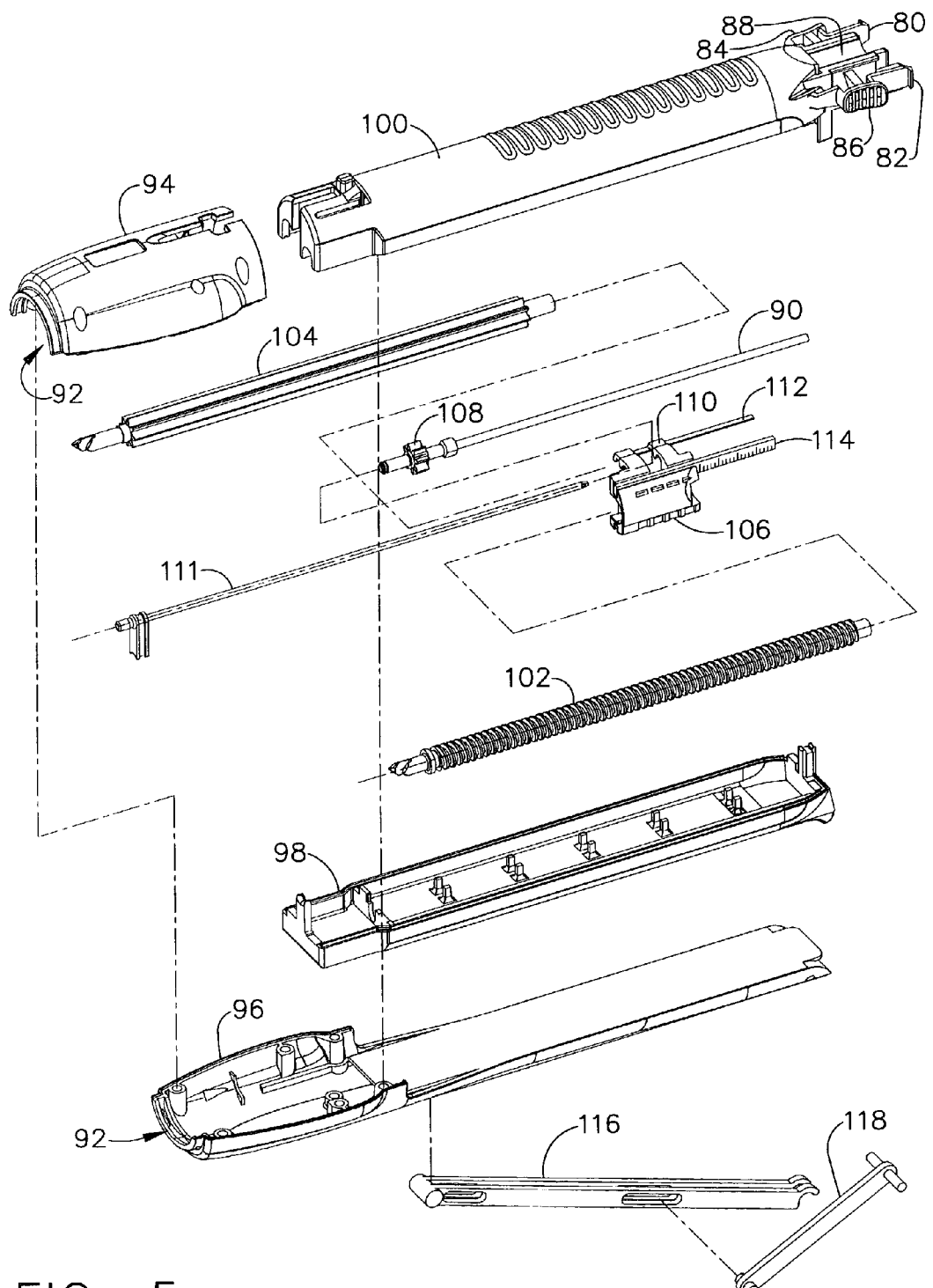
FIG. 5 is an exploded isometric view of the biopsy instrument handle.

FIG. 5 depicts a disassembled biopsy handle 36 that contains the means for translating and rotating a cutter 90 within the cutter lumen 56. It will be appreciated that two rotating mechanical power sources are presented to the proximal end of the biopsy handle 36 through the power cord 18 to provide the independent translation and rotation motions. These two rotating mechanical power sources enter through a cord opening 92 defined between a removable shell 94 and a bottom shell 96, the two held together by screws. The removable shell 94 is removed when assembling a power cord 18 to the handle 36. A lower gear housing 98 is supported upon the bottom shell 96 and cooperates with a top shell 100 to constrain movement of an elongate drive screw 102, an elongate axial screw 104 and cutter carriage 106. In particular, both screws 102, 104 are allowed to rotate, positioned parallel to one another and the longitudinal axis of the cutter lumen 56. Each screw 102, 104 is driven by a respective power source from the power cord 18. The drive screw 102 passes through the carriage 106 and interacts with corresponding ridges therein to impart a longitudinal translation corresponding to the direction and rate of rotation of the drive screw 102.

In some applications, a single rotary power source may be used as an alternative to two independent rotating mechanical power sources. A transmission mechanism at the biopsy handle 36 may convert the single rotary power source into the two motions, translation and rotation. As yet another alternative, the single rotary power source may directly supply both a translation and rotary motion. Such a translating and rotating power cable would be coupled to the cutter 90 to directly control its movement.

The cutter 90 is an elongate tube with a sharpened distal end for cutting tissue presented within the distal end of the cutter lumen 56. The proximal end of the cutter 90 includes a cutter gear 108 that is exposed through a gear window 110 of the carriage 106 to mesh with the axial screw 104 for axial rotation of the cutter 90. A tissue remover 111 is a tube that is fixedly aligned with the longitudinal axis to enter the proximal end of the cutter 90. The tissue remover 111 extends up to the sample window 88 and has a vacuum selectably applied to it by the control module. Thus, when the cutter 90 is retracted, vacuum from the tissue remover 111 draws the sample to the distal end of the cutter 90 for retraction to the sample window 88, whereupon the sample encounters the tissue remover 111 and is dislodged for exiting the biopsy tool 14.

The carriage 106 includes distally projected guides 112, 114 that advantageously take-out slack between biopsy handle 36 and the probe housing 46, as well as providing indicia to the surgeon as to the depth of translation of the cutter 90. Taking out slack between the assembled parts of the handle 36 and housing 46 advantageously minimizes the deadzone length of the distal end of the needle 58. The cutter 90 should completely translate past the sample port 60 in order to reliably cut a sample. To ensure a full cut, the cutter 90 should translate the maximum distance expected for the assembly. If variation exists in manufacturing tolerances between the engagement components, then a further distance has to be included in the cutter lumen 56 distal to the sample port 60 to accommodate the over-travel. Thereby, the needle tip 62 must be advanced farther than desirable in some instances, preventing placement of the sample port 60 near critical body tissues. At or near full travel, the guides 112, 114 contact the probe housing 46, causing movement of the housing 46 to its maximum, distal position. Thus, critical dimensioning to minimize tolerance build-up is simplified.

FIG. 5 also depicts a brace 116 and brace arm 118 that are employed in one version of the localization fixture 16 to support the weight and maintain the alignment of the handle 36. Thereby, flexure of the assembly is avoided that may place a load on the probe assembly 38, and thus unwanted movement of the needle 58 from the desired biopsy site location.

Figures 6, 7:
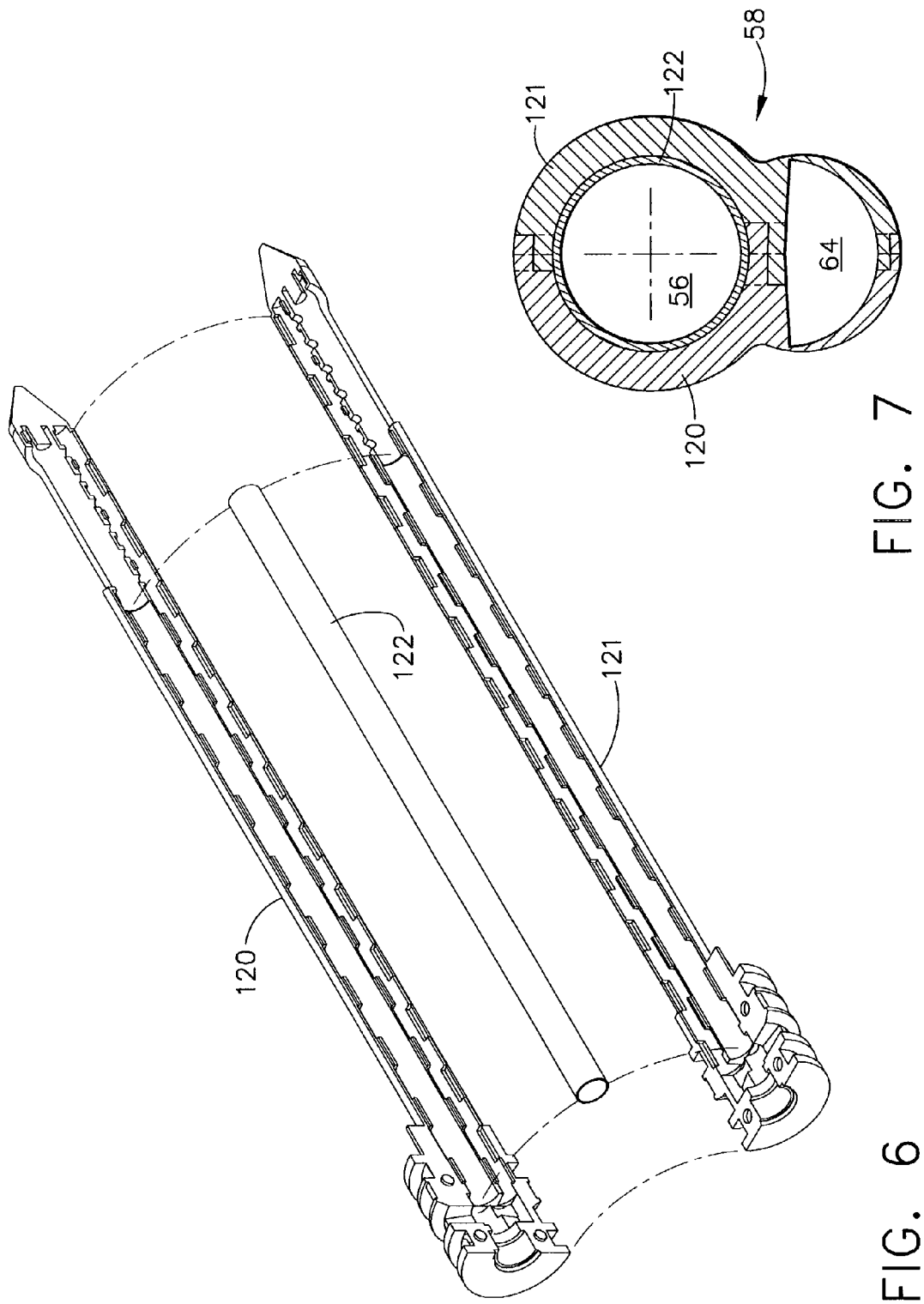
FIG. 6 is an exploded isometric view of the probe of the biopsy instrument of FIG. 4.
FIG. 7 is a transverse cross section of the probe of the biopsy instrument of FIG. 4 along lines 7-7.

FIGS. 6-7 depict the needle 58 of FIG. 4 and described more fully in the aforementioned application Ser. No. 10/021,680, entitled "AN MRI COMPATIBLE SURGICAL BIOPSY DEVICE". In particular, elongated needle 58 is formed from a left body member 120 and a right body member 121 on either side of the longitudinal axis. The edges of the halves 120 and 121 are gated for easy part filling, and the edges are stepped with ridges that allow the two halves 120 and 121 to attach together with ease. The two halves 120, 121 are adhesively attached to one another. A cutter tube liner 122 is inserted between the two halves 120, 121 to provide a smooth surface for the cutter 90, especially by preventing adhesive from entering the cutter lumen 56 during assembly.

Figure 8:
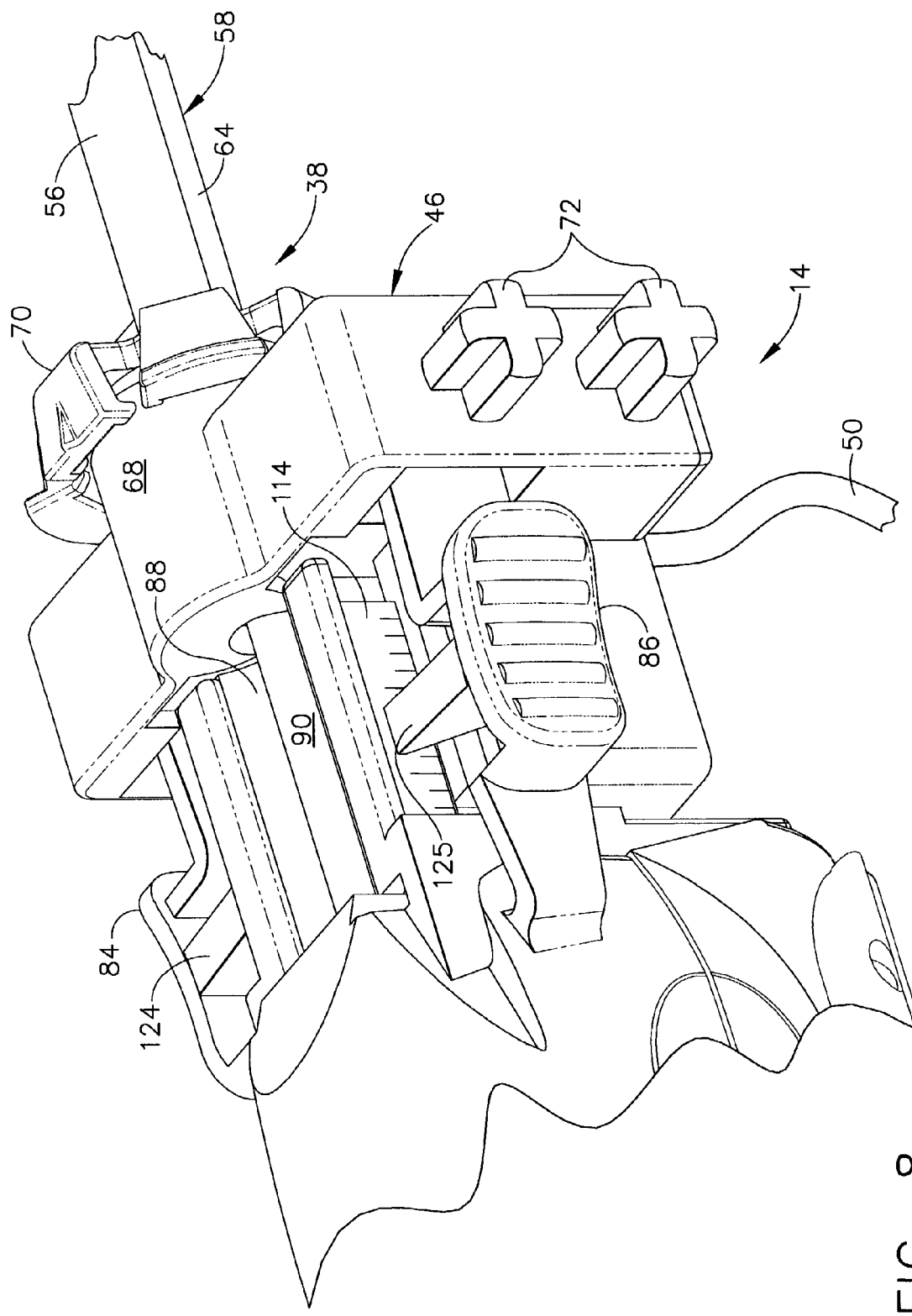
FIG. 8 is an enlarged isometric view of the interface between the handle and probe housing illustrating the visual confirmation elements that indicate the position of the distal end of the cutter.

FIG. 8 shows an enlarged view of the engagement of the handle 36 to the probe housing 46, with the advanced cutter 90 evident through the window 88. In addition, the guides 112, 114 are advanced almost into contact with the probe housing 46, indicating that the distal end of the cutter 90 is approaching its furthest translation. The guides 112, 114 contact the probe housing 46 when at or near this extreme to take-out any tolerance. Indicia on the side of the guides 112, 114 may be referenced by the surgeon to determine the position of the cutter. Also shown in more detail is hooked locking tabs 80, 82 entering the probe housing 46, the thumb wheel 70 used to rotate the needle 58, and the vacuum lumen access conduit 50 used to evacuate or otherwise access the vacuum lumen 64.

FIGS. 8-10 show that each grip 84, 86 includes a respective inwardly projecting member 124, 125 that contact the guides 112, 114 when the cutter 90 is distally advanced, thereby preventing removal of the handle 36. In FIG. 9, the cutter 90 is retracted, allowed the depression of the grips 84, 86, unlocking the hooked locking tabs 80, 82 from the probe housing 46. In FIG. 10, cutter carriage 106 is advanced, the guides 112, 114 are contacting the probe housing 46, thereby removing any longitudinal gap between the hooked locking tabs 80, 86 and the probe housing 46.

FIGS. 11-14 depicts a localization fixture 16 that includes means for accurately positioning the probe assembly 38 and supporting the biopsy handle 36. In particular, a localizer support frame 126 is formed from the compression plate 42 in a hinged, orthogonal relation to a horizontal slide plate 128, both laterally attached to one another by gussets 130, 132. Rods 134, 136 horizontally pass through the compression plate to adjustably attach to the medial compression plate (not shown) for compressing the patient's breast. Apertures, depicted as parallel rows of slots 138, in the compression plate 42 are provided to obtain access to a desired biopsy site location while providing enough remaining structure in the compression plate 42 for adequate contact with the patient's breast. Alternatively, the apertures may be a series of holes aligned both vertically and horizontally, parallel columns of slots, or a large opening of other shapes. As yet a further alternative, portions of the compression plate 42 may be permeable to allow an aperture to be formed as needed.

The desired biopsy site location is stereotopically determined during an MRI scan with reference to a fiducial marker 140 that presents a small artifact. The fiducial marker 140 is contained within a fiducial marker holder 142 that may be placed at a convenient location on the compression plate 42, accurately placed with reference to indents spaced along the slots 138. Alternatively, the fiducial marker may be embedded or affixed to the compression plate 42.

The localizer support frame 126 defines and provides the guide for positioning the probe assembly 38. The X-Y-Z axes are defined with regard to the slots 138 and compression plate 42. In particular, the vertical dimension, or Z-axis, and horizontal dimension, or X-axis, are defined by the surface of the compression plate 42. The depth dimension, or Y-axis, is defined as distance away from the plane of the compression plate 42. The horizontal slide plate 128 includes laterally aligned front and back rails 144, 146 for setting the X-axis coordinate. Horizontal indicia 148 along the front rail 144 give the surgeon an accurate measurement of the position of a probe assembly mounting device 150.

A first version of the mounting device 150 is depicted that uses a single vertical pedestal 152 to position and support the probe assembly 38. In addition, the biopsy handle 36 is supported by a brace 116, which is connected to the proximal underside of the handle 36 and to a handle support rod 156 that is slid through a rod hole 158 at the corresponding side of the vertical pedestal 152. The appropriate height for the brace 116 is determined by selecting one of a range of slots arrayed along the underside of the handle, thereby pivoting the brace 116 about a brace arm 118 whose first end slidably pivots within a slot 162 in the middle of the brace 116 and second end attaches to the distal end of the handle 36.

Figure 11:
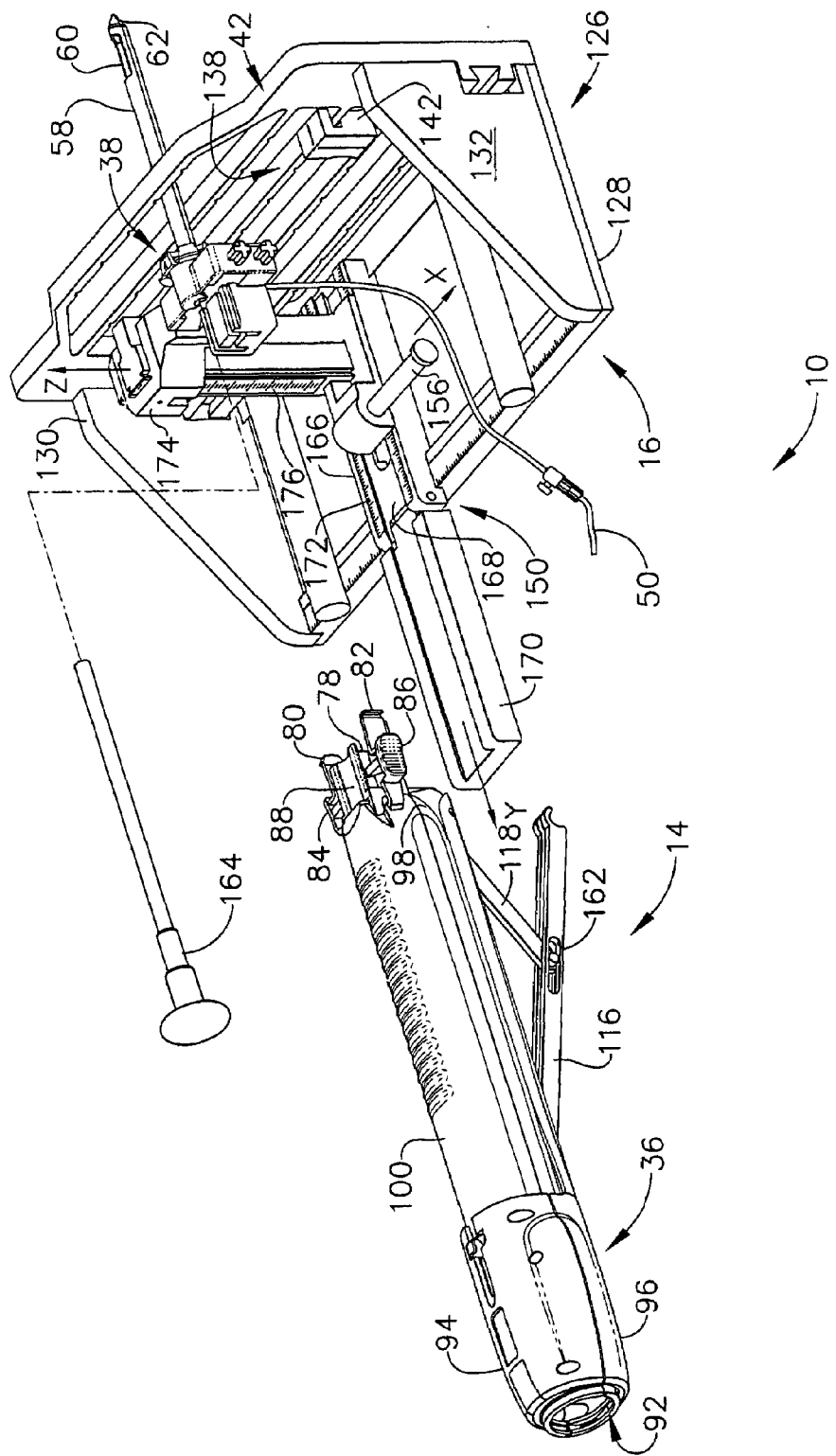
FIG. 11 is an isometric view of the biopsy instrument with the handle portion disconnected from a tower/bracket localization fixture and probe assembly.
Figure 12:
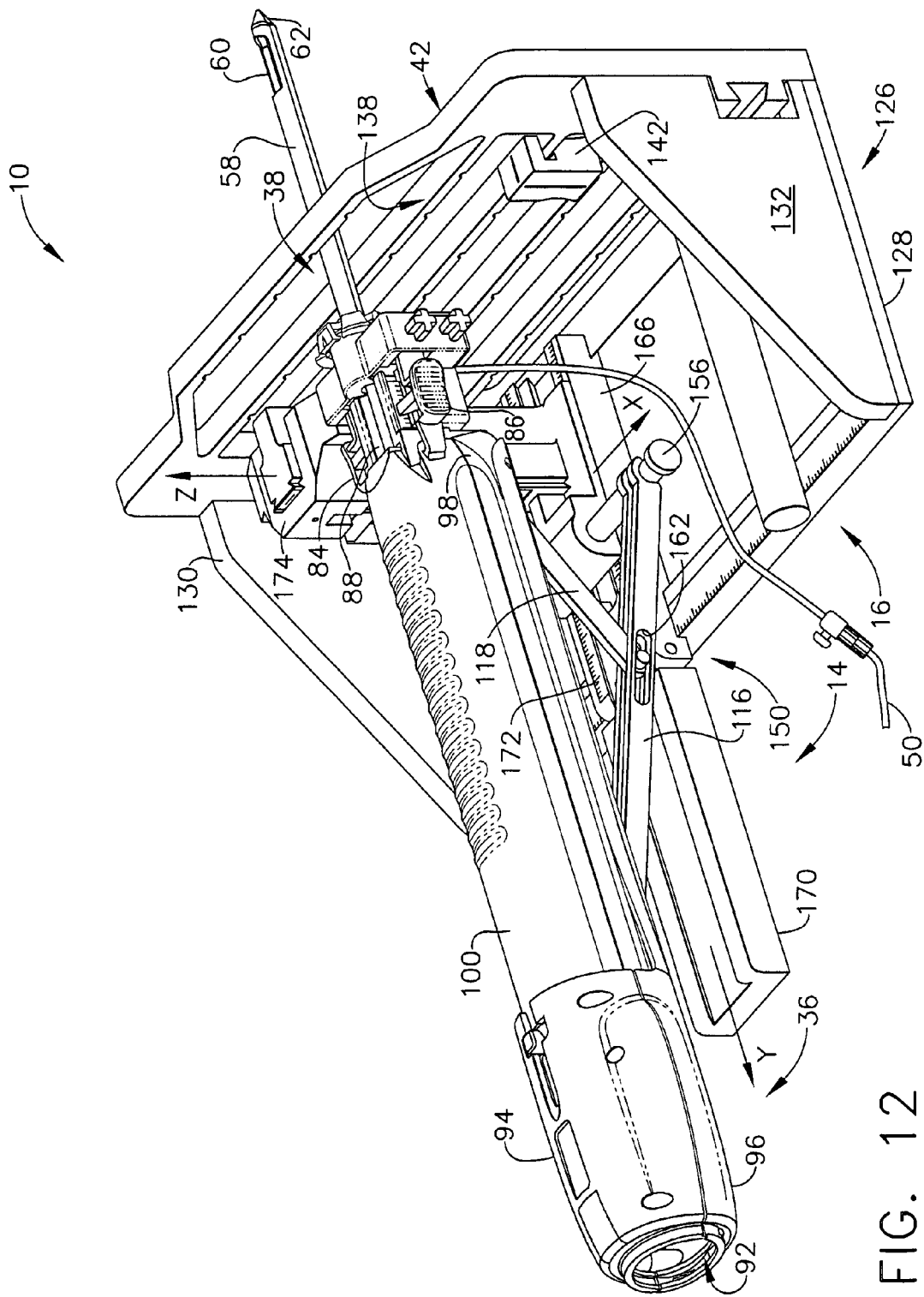
FIG. 12 is an isometric view of the biopsy instrument mounted to the tower/bracket localization fixture of FIG. 11.
Figure 13:
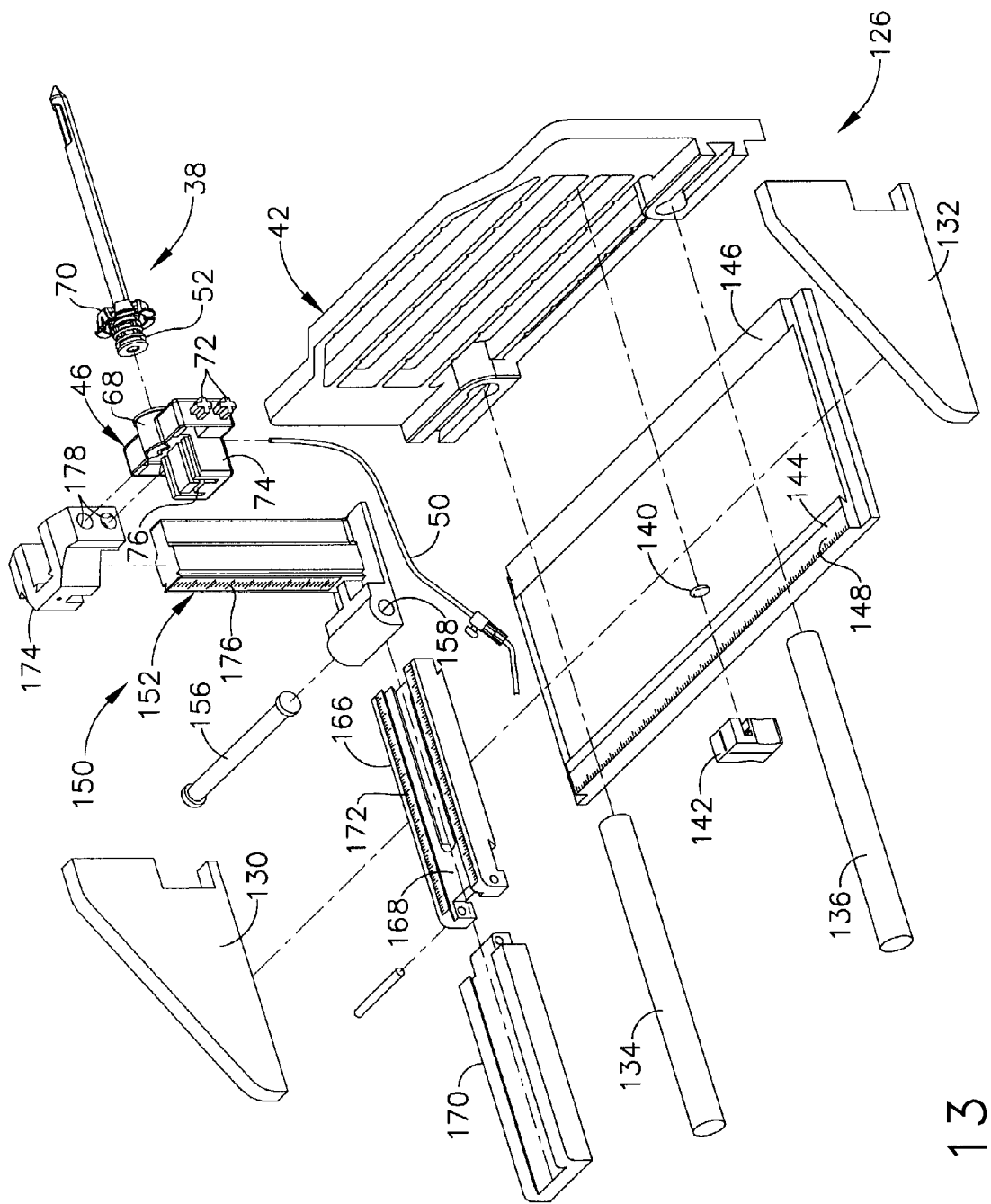
FIG. 13 is an exploded isometric view of the tower/bracket localization version of the localization fixture and probe assembly of the biopsy instrument.
Figure 14:
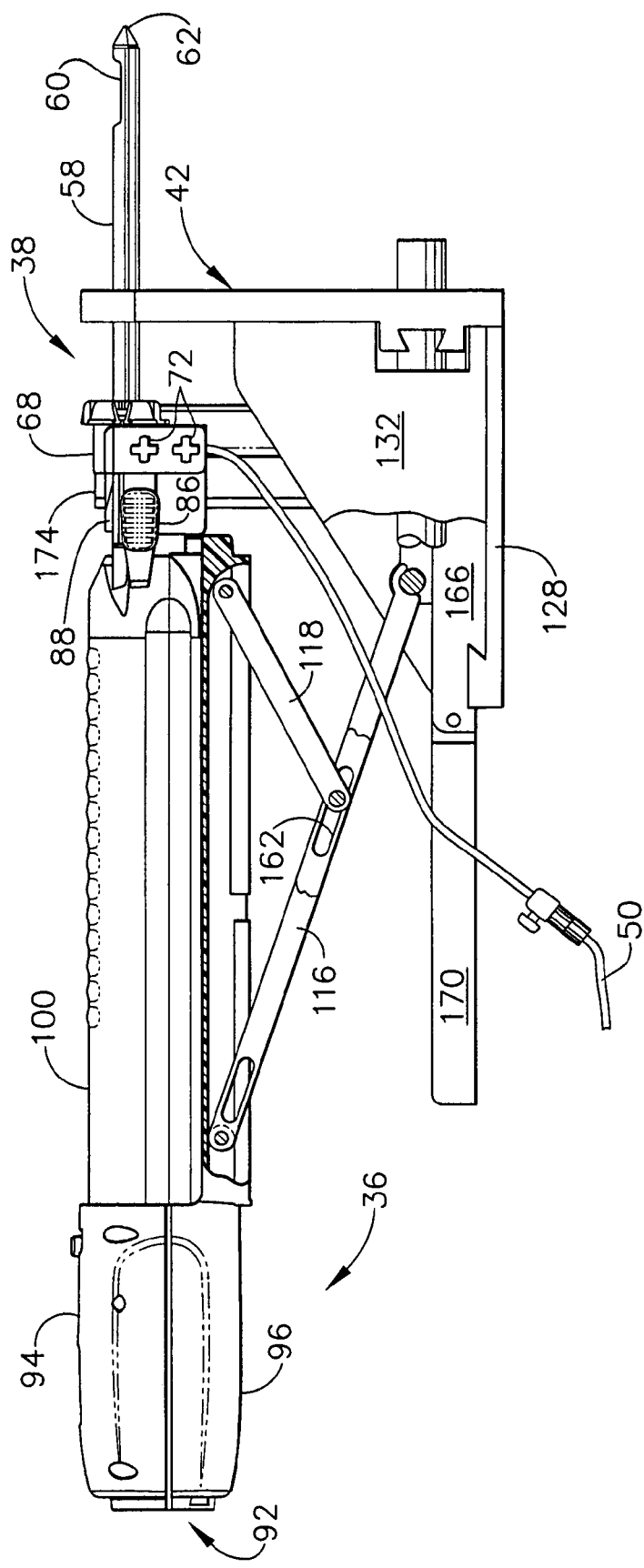
FIG. 14 is a side elevation view of the biopsy instrument in partial section to illustrate a tower/bracket support for stabilizing the handle and probe assembly of the biopsy instrument.

With the handle 36 detached from the probe assembly 38 as depicted in FIG. 11, an obturator stylet 164 is slid into the cutter lumen 56 to close the cutter port 88. The stylet 164 may have radially-oriented through holes near its distal end to maintain fluid communication between the vacuum lumen chamber 64 and cutter lumen 56. Alternatively, the stylet 164 may be partially withdrawn, allowing the cutter port 88 to be in fluid communication with the conduit 50.

A slide 166 includes a grooved underside to horizontally slide on rails 144, 146 of the slide plate 128. The slide 166 also includes a central channel 168 oriented in the Y-axis depth dimension to guide the pedestal 152 as it slides in the Y-axis direction. Sufficient range of motion in depth is achieved with a pivoting depth slide 170, aligned and pivotally attached to the slide 166. With the pivoting depth slide 170 in its lowest, horizontal position, the pedestal 152 may be slid outward sufficiently for the probe assembly 38 to be out of the compression plate 42. With the pedestal 152 distally slid onto the slide 166, the pivoting depth slide 170 may be pivoted upward or otherwise removed. Depth indicia 172 along the central channel 168 give the surgeon an indication of the insertion depth of the probe assembly 38.

A vertical slide 174 slides on the pedestal 152 for vertical positioning along the Z-axis, with a measurement provided by vertical indicia 176 on the pedestal 152. Holes 178 on each lateral side of the vertical slide 174 allow mounting of the probe housing 46 on either side by insertion of attachment probes 72.

Figure 15:
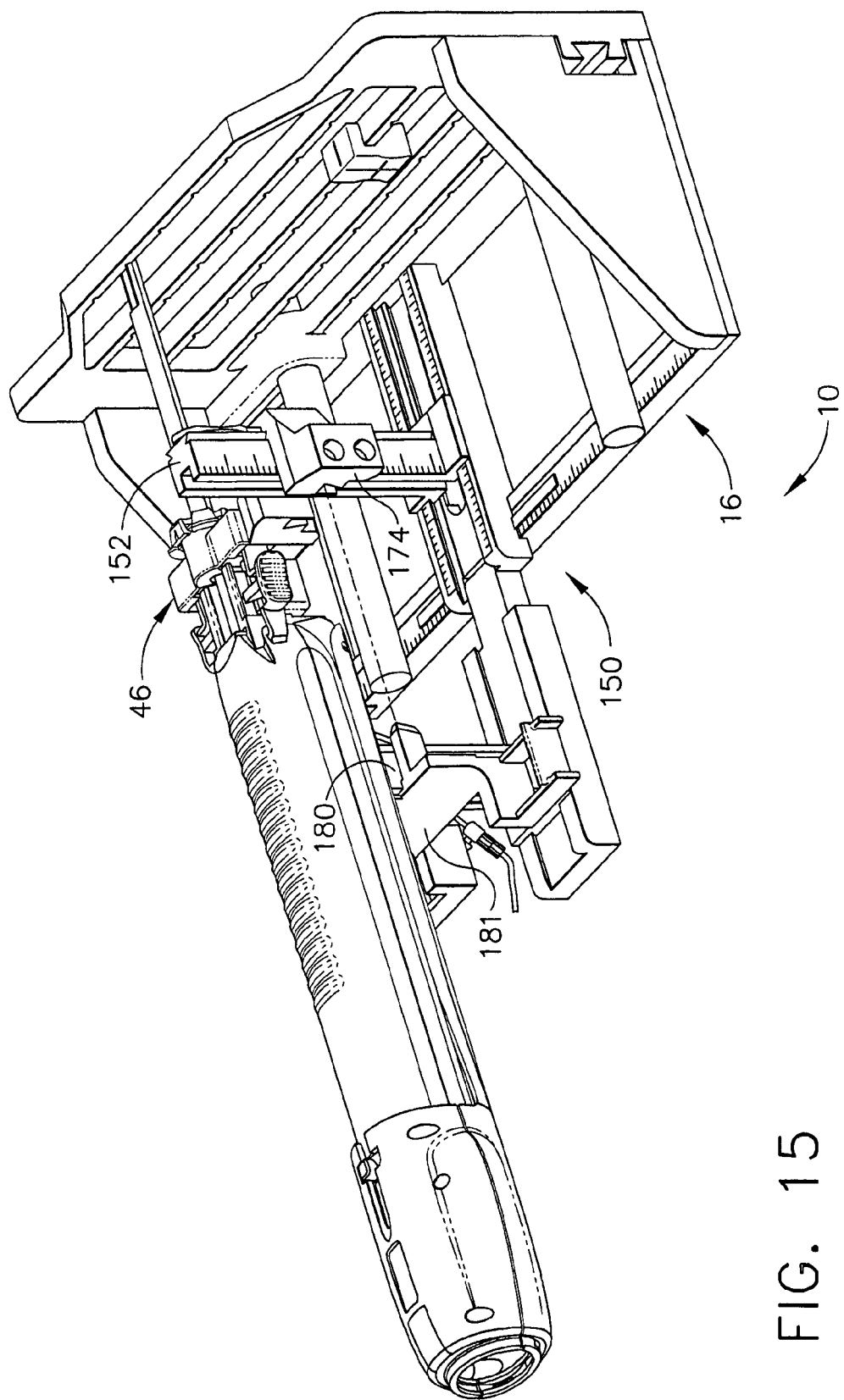
FIG. 15 is a side elevation view of the dual tower support version of the localization fixture positioning a detachable probe assembly with its dual lumens closed by a vacuum conduit and an obturator stylet.
Figure 16:
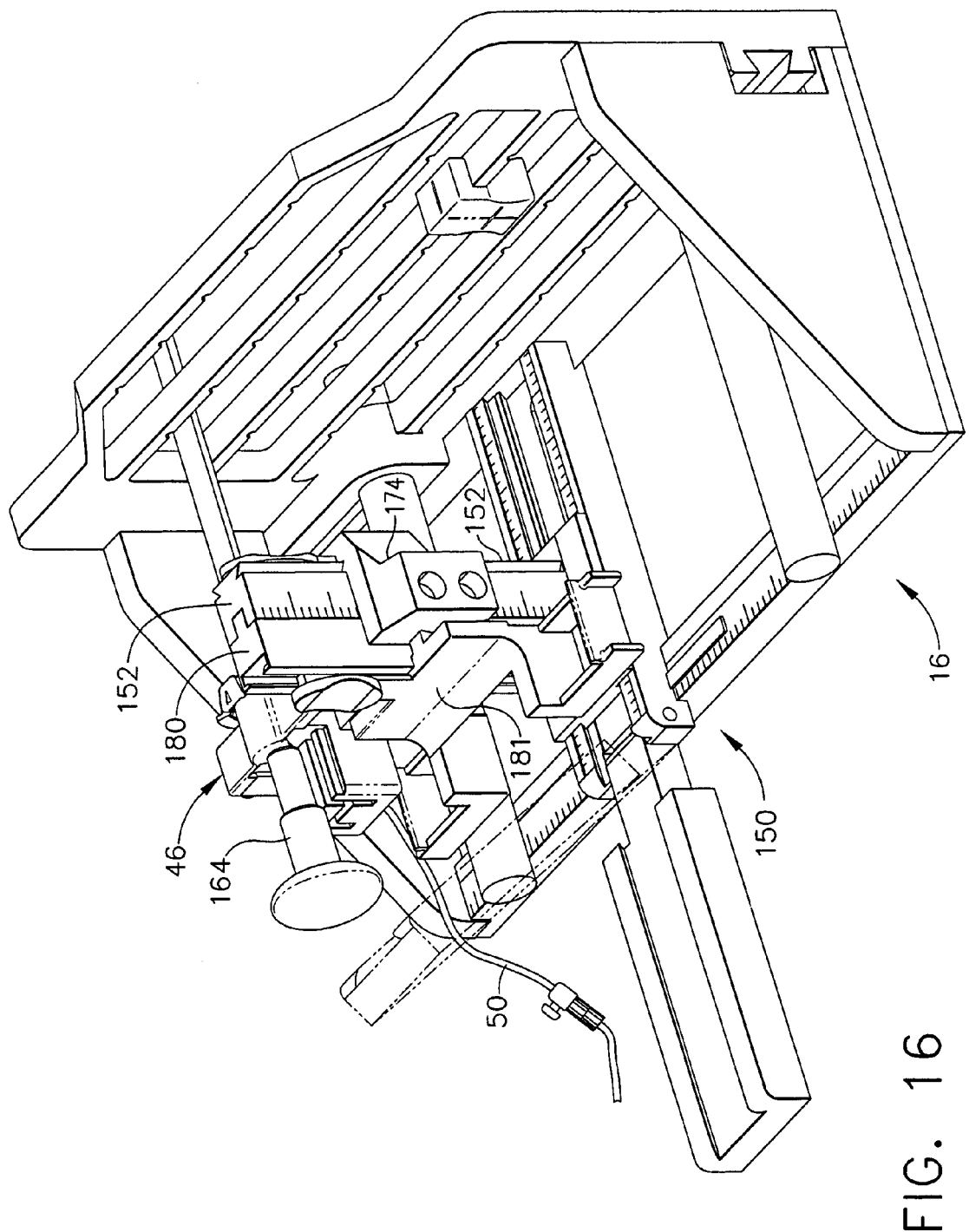
FIG. 16 is an isometric view of the biopsy instrument mounted to a dual tower localization fixture.

FIGS. 15-16 depict a second version of the mounting device 150 that uses a second vertical pedestal 180 in lieu of a brace assembly to support the handle 36. The probe housing 46 is also depicted as attached to the opposite side of the first vertical pedestal 152. A second vertical slide 181 of the second vertical pedestal 180 contacts the first vertical slide 174, as shown in FIG. 16, so that setting the vertical height for both is accomplished in one step. Each vertical slide 174, 181 moves in a ratchet fashion against its respective vertical pedestal 152, 180, and thus remains in position after being separated from one another as shown in FIG. 15. Moreover, the close nesting of the two vertical pedestals 152, 180 enhances the ability to minimize the proximal displacement of the localization fixture 16 when used within the close confines of a closed MRI magnetic bore 24. It will be further appreciated that the second vertical slide 181 includes a shaped area that engages the underside of the handle 36 in such a way as to correctly align the handle 36 at the same X-axis horizontal dimension as the probe assembly 38.

Figure 17:
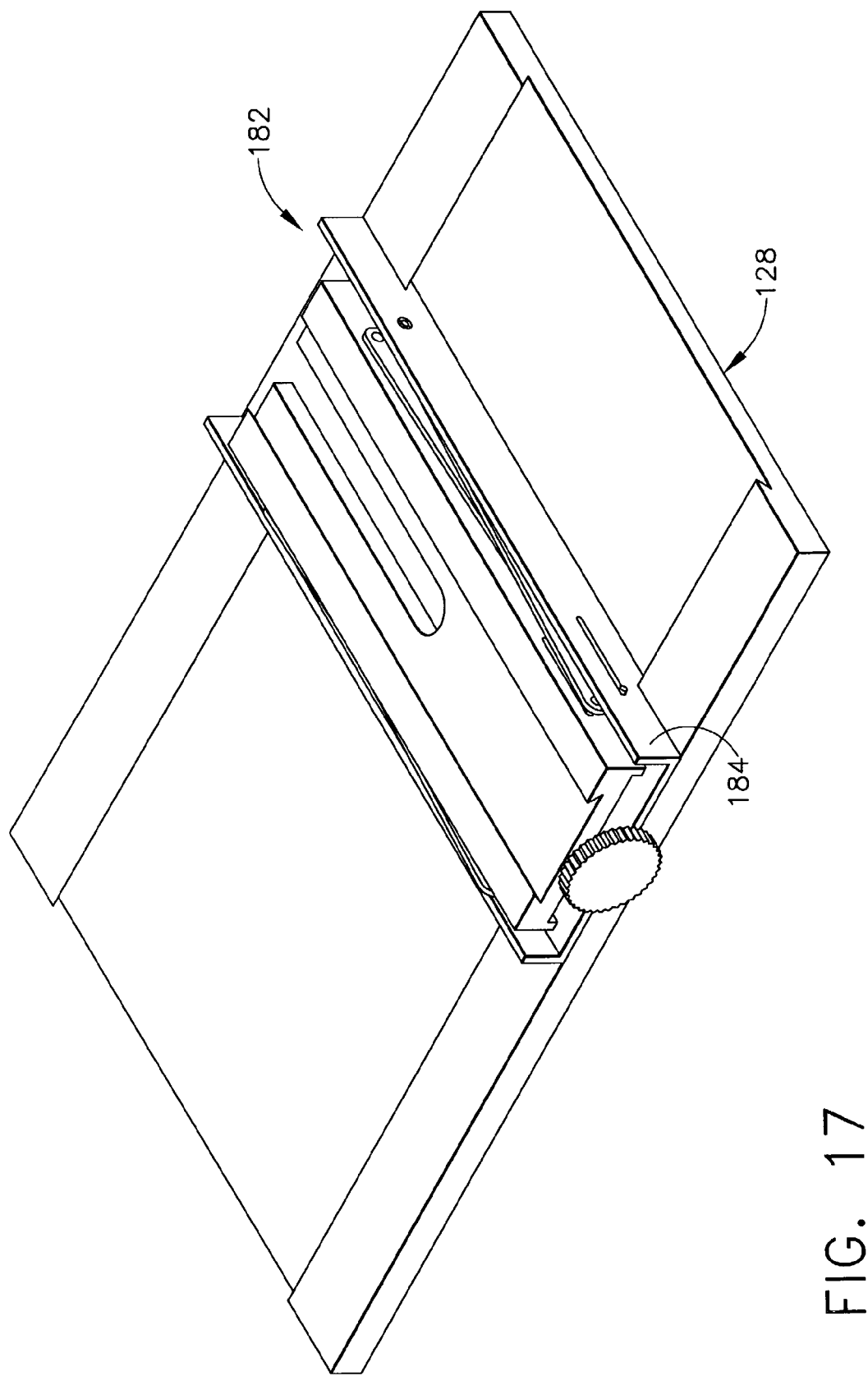
FIG. 17 is an isometric view of the slide plate of a localization fixture guiding a scissors support in a lowered position for vertically orienting a biopsy instrument.
Figure 18:
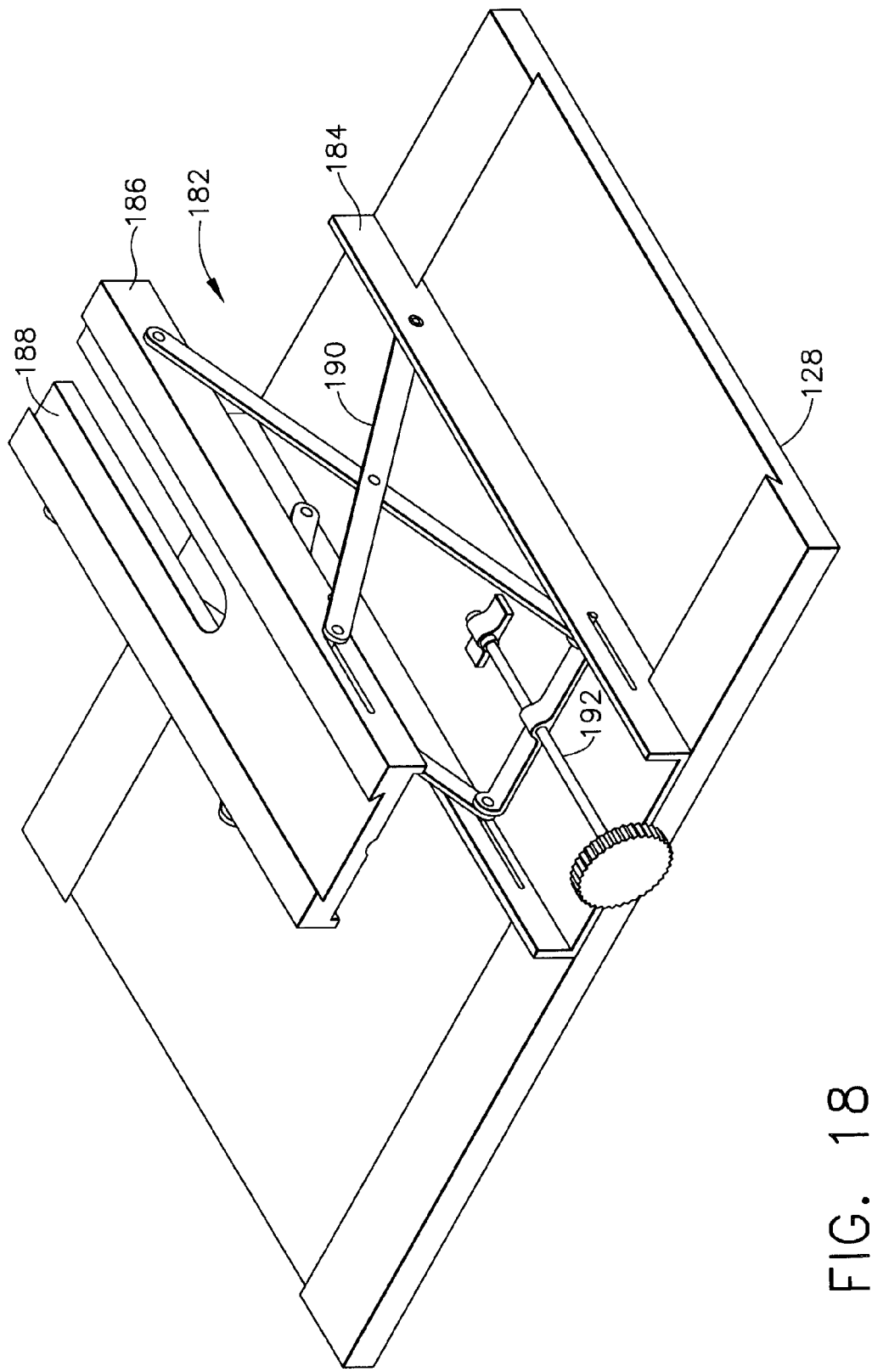
FIG. 18 is an isometric view of the slide plate of a localization fixture guiding the scissors support in a raised position for vertically orienting a biopsy instrument.

FIGS. 17-18 depict a third version of the mounting device 150 wherein the slide 166 and pedestal 152 are replaced with a scissors table assembly 182 that includes a first slide 184 for horizontal movement on a slide plate 128 and a second slide 186 for vertical movement relative to the slide plate 128. Similar to the slide 166 of FIGS. 11 and 13 having the central channel 168, the second slide 186 of FIGS. 17-18 has a top channel 188. With particular reference to FIG. 18, a pair of scissors braces 190 are extended when drawn together with a screw 192, thereby elevating the second slide 186 with respect to the first slide 184. It will be appreciated that the third version of the mounting device 150 advantageously provides a level support for both the detachable probe assembly 38 as well as the biopsy handle 36 without having to perform two vertical adjustments, as well as not having to perform two separate attachments for each of the handle 36 and probe assembly 38.

Figure 19:
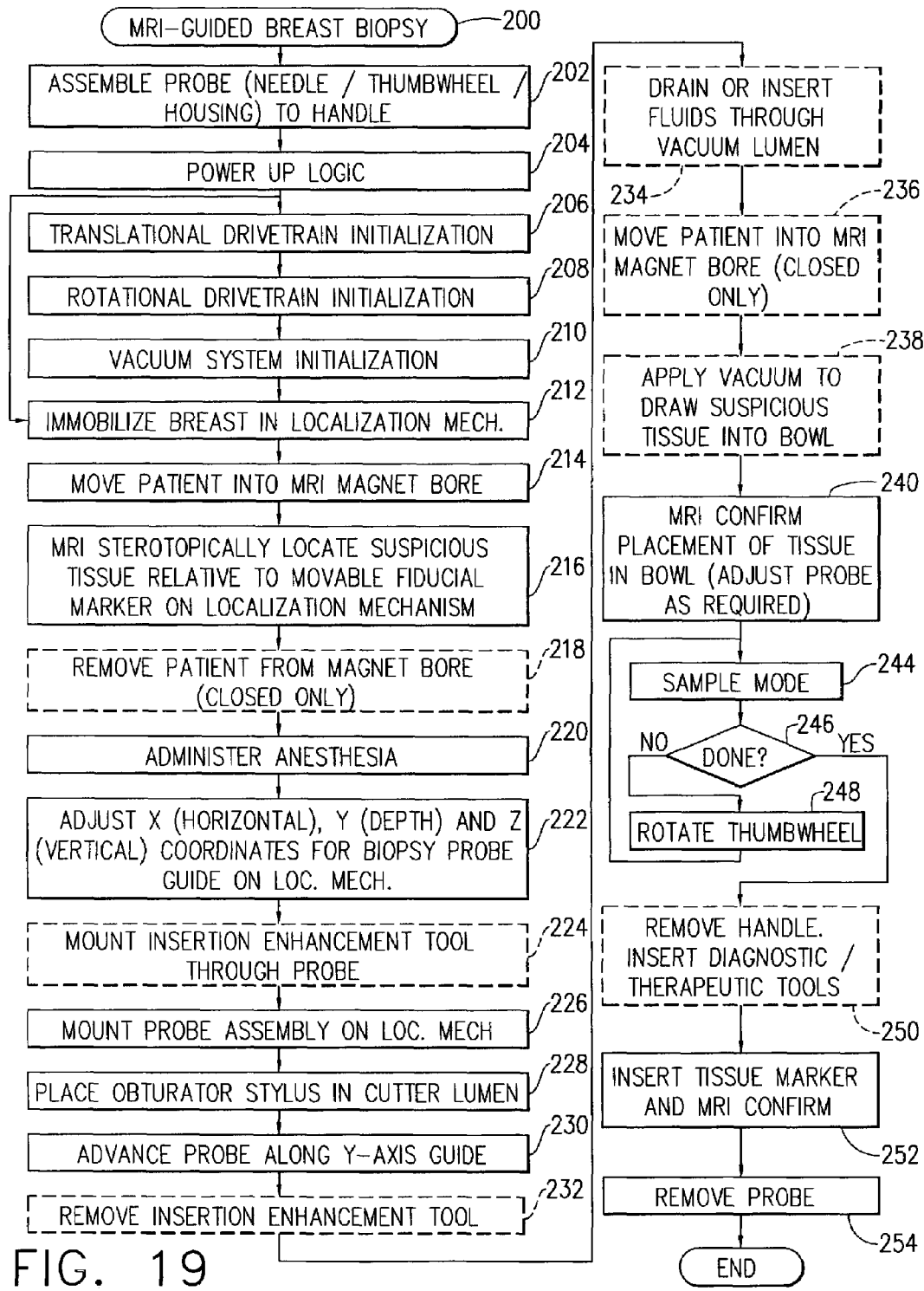
FIG. 19 is a sequence of clinical operations for using the detachable MRI-guided biopsy instrument of FIG. 1 in both open and closed MRI machines.

FIG. 19 depicts a sequence of operations, or method 200, for performing an MRI-guided breast core biopsy that accurately and quickly performs a core biopsy even in a closed MRI. Moreover, the method takes full advantage of the stereotopic location information rendered from the MRI scan to position an MRI compatible core biopsy probe without the necessity of continuous imaging of the distal tip of the biopsy probe.

Prior to performing a clinical breast biopsy, the equipment is initialized to ensure proper function. Thus, in block 202, the probe that comprises a needle, thumb wheel and housing is assembled with the handle. The assembled biopsy tool is connected via a power cord to a control module and the system is powered up, initiating power up logic in the control module (block 204). Parameters for rotation speed and translation distances are loaded. If the control module determines that the system has not been powered up recently, such as 60 minutes, then initialization logic is performed. Thus, translational drivetrain initialization is performed (block 206); rotational drivetrain initialization is performed (block 208); and vacuum system initialization is performed (block 210). If initialization is not required, then blocks 206-210 are bypassed.

Then, the patient's breast is immobilized in the localization mechanism (block 212) and the patient is moved into the MRI magnet bore (block 214). An MRI scan is performed to stereotopically locate suspicious tissue with reference to a movable fiducial marker on the localization mechanism (block 216). For a closed MRI magnet bore, the patient is then removed (block 218), which is not necessary for an open bore. Anesthesia is administered prior to the minimally invasive vacuum assisted core biopsy procedure (block 220). Using the X-Y-Z positioning capabilities of the localization mechanism, the positioning guides on the localization mechanism are positioned for insertion to the predetermined biopsy site (block 222).

Optionally, insertion may be enhanced by use of an insertion tool installed through the probe assembly 38 (block 224). For instance, an ultrasonic cutting tip, extender, and outer tube assembly may be inserted through the probe assembly 38 through a slot in the needle tip 62, or exiting from the sample port 60 to be snapped onto the needle tip 62. This could be accomplished with a housing on the ultrasonic device that is configured to snap onto the needle 58, similarly to how a trocar obturator snaps onto the trocar cannula. Then, the ultrasonic tip is energized prior to insertion into the patient.

The probe assembly is mounted on the localization mechanism (block 226) at the designated X-Z coordinate and with the mounting device withdrawn along the depth axis. The cutter lumen is sealed with an obturator stylet (block 228), if not otherwise sealed by a tool in block 224. The vacuum lumen may be similarly sealed (e.g., stopcock attached to vacuum lumen access conduit 50) or be used to aspirate fluid and tissue during insertion. Then the probe is advanced along the Y-axis, guided by the localization mechanism to avoid misalignment (block 230). Once in place, if an insertion enhancement tool was installed in block 224, then this tool is withdrawn through the cutter lumen of the probe assembly (block 232).

With the probe in place, various fluid transfers may advantageously take place through the probe assembly (block 234). For example, vacuum may be applied through the vacuum lumen with the sample port exposed to drain any hematoma or air bubble formed at the biopsy site. Treatment fluids may be inserted directly to the biopsy site, such as anesthesia or MRI contrast agent. If the patient is to be scanned in a closed magnet bore, then the patient is moved back into the bore for scanning (block 236). In addition, vacuum may optionally be applied to the biopsy site to draw in suspicious tissue into the bowl of the sample port for confirmation prior to cutting the sample (block 238). Then, the MRI scan is performed to confirm placement of tissue in the bowl of the probe assembly, and adjustment of the probe assembly placement and re-scans are performed as required (block 240).

Sample mode is selected through the control module to perform the sequence of steps to translate and rotate the cutter according to predetermined settings, with vacuum assist to draw in the sample and to retract the sample along with the cutter to the sample window (block 244). If more samples at this biopsy site are required for diagnostic or for treatment purposes (block 246), then the thumb wheel is rotated to reorient the sample port to another angle (block 248), and sample mode is performed again by returning to block 244.

After the core biopsy is performed, the probe assembly provides an excellent opportunity for other minimally invasive diagnostic procedures and treatments without the necessity for another insertion. If the biopsy handle is installed, such as in an open MRI magnet bore, the handle is removed so that the detachable probe assembly may be accessed (block 250). Examples of tools that may be inserted through the probe assembly include: (1) gamma detectors; (2) energized tunneling tips to reduce tunneling forces; (3) inserts to aid in reconstruction of removed tissue (e.g., one or two sided shaver inserts); (4) spectroscopy imaging devices; (5) general tissue characterization sensors {e.g., (a) mammography; (b) ultrasound, sonography, contrast agents, power Doppler; (c) PET and FDG ([Flourine-18]-2-deoxy-2-fluoro-glucose); (d) MRI or NMR, breast coil; (e) mechanical impedance or elastic modulus; (f) electrical impedance; (g) optical spectroscopy, raman spectroscopy, phase, polarization, wavelength/frequency, reflectance; (h) laser-induced fluorescence or auto-fluorescence; (i) radiation emission/detection, radioactive seed implantation; (j) flow cytometry; (k) genomics, PCR (polymerase chain reaction)-brca1, brca2; (l) proteomics, protein pathway}; (6) tissue marker sensing device; (7) inserts or devices for MRI enhancement; (8) biochips on-a-stick; (9) endoscope; (10) diagnostic pharmaceutical agents delivery devices; (11) therapeutic anti-cancer pharmaceutical agents delivery devices; (12) radiation therapy delivery devices, radiation seeds; (13) anti-seeding agents for therapeutic biopsies to block the release of growth factors and/or cytokines (e.g., chlorpheniramine (CPA) is a protein that has been found to reduce proliferation of seeded cancer sells by 75% in cell cultures.); (14) fluorescent tagged antibodies, and a couple fiber optics to stimulate fluorescence from a laser source and to detect fluorescence signals for detecting remaining cancer cells; (15) positive pressure source to supply fluid to the cavity to aid with ultrasound visualization or to inflate the cavity to under the shape or to reduce bleeding; (16) biological tagging delivery devices (e.g., (a) functional imaging of cellular proliferation, neovacularity, mitochondrial density, glucose metabolism; (b) immunohistochemistry of estrogen receptor, her2neu; (c) genomics, PCR (polymerase chain reaction)-brca1, brca2; (d) proteomics, protein pathway); and (17) marking clips.

Then, a tissue marker is inserted through the probe assembly so that subsequent ultrasonic, X-ray, or MRI scans will identify the location of the previous biopsy (block 252) and the probe is removed (block 254).

Figure 20:
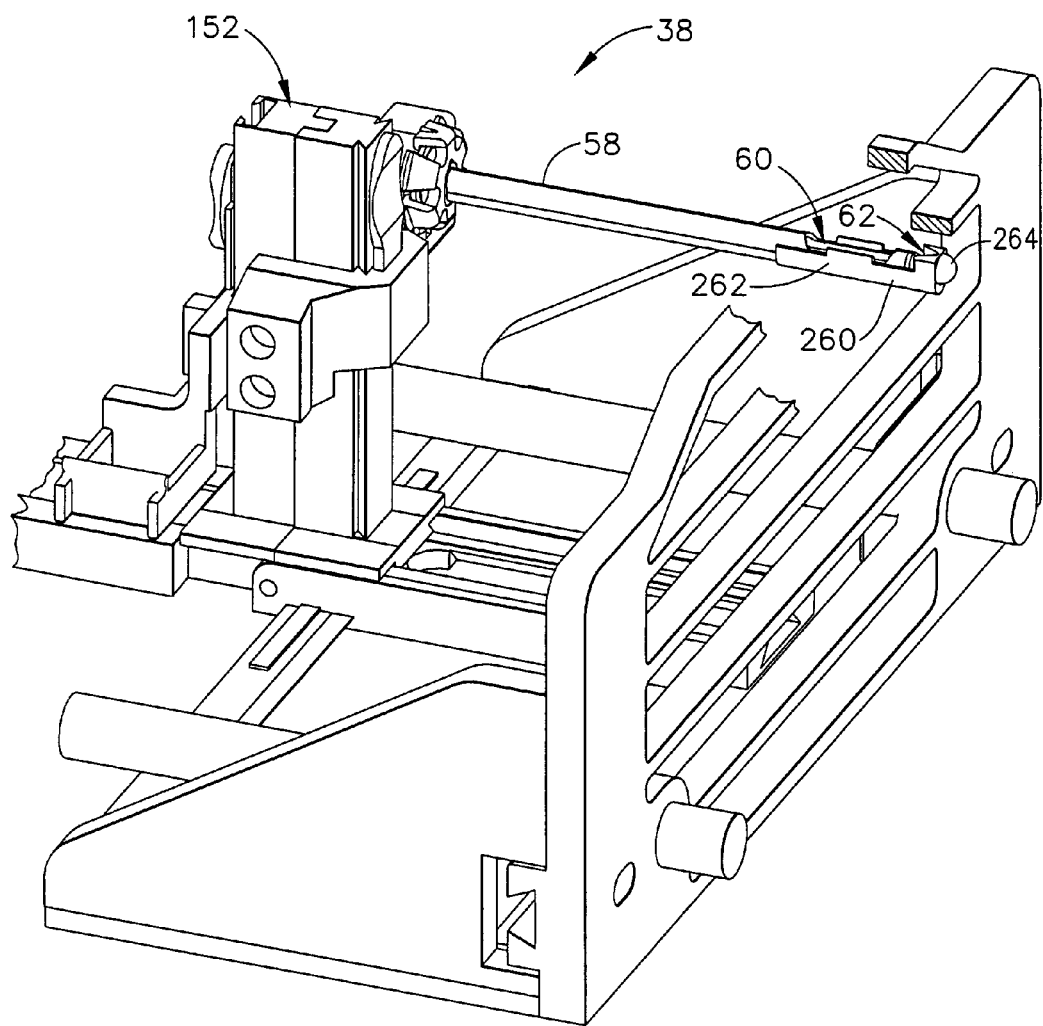
FIG. 20 is an isometric view of a tip protector mounted onto a needle tip of the detachable probe assembly of FIG. 11.
Figure 21:
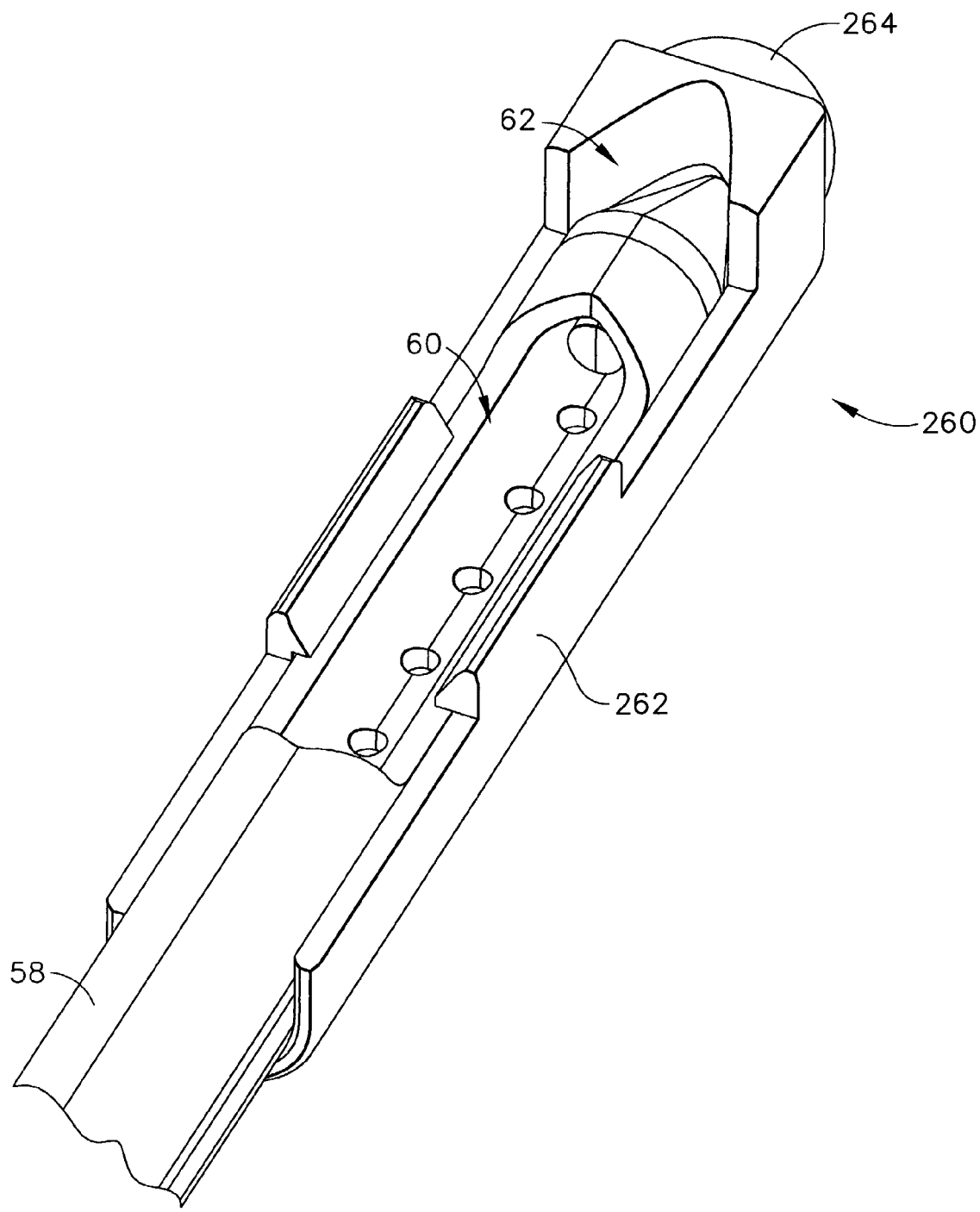
FIG. 21 is an isometric detail view of the trip protector of FIG. 20.

FIGS. 20-21 depict a tip protector 260 that advantageously protects the needle tip 62 of the probe assembly 38 prior to insertion into tissue and simplifies localization of the probe assembly 38 in some instances. Furthermore, the tip protector 260 does not interfere with pre-clinical setup procedures (e.g., testing for vacuum leaks). In particular, the tip protector 260 includes an attachment member 262 with clips onto the needle 58 without obstructing the sample port 60. A distal portion of the tip protector completely encompasses the needle tip 62 with a protection member, depicted as a hemispheric disk 264, that may be placed in contact with a patient's breast without discomfort. In addition, in some applications the hemispheric disk 264 may be comprised of or include an MRI artifact producing material, such as those described above. Since the hemispheric disk 264 is MRI scanned outside of the patient's breast, a stronger artifact may be presented to aid in quickly locating the artifact without obscuring the suspected lesion.

With a novel fiducial marker integrated into the tip protector 260, there is potentially one less step in the localization process for operators that prefer to position fiducial marker at the closest insertion point to a suspected lesion prior to insertion. Procedurally, with the tip protector 260 in place, the operator would attach the probe assembly 38 onto the pedestal 152 and move the probe assembly 38 up against the breast tissue in the vicinity of where they believe the suspicious tissue to be, based on an earlier diagnostic image. Next, when the distance from this fiducial marker to the lesion is calculated, the "delta" distances are based on where the probe is currently positioned. There is a fixed offset along the Y axis to account for the distance from the fiducial to the middle of the bowl. The attachment member 262 accurately locates the hemispheric disk 264 so that this Y-axis offset is predictable. This would be more intuitive because the delta positions are from where the probe is currently located.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, although the detachable probe assembly provided numerous benefits, it will be appreciated aspects of the present invention may be directed to a single piece biopsy tool. For example, access to the cutter lumen for diagnostic and therapeutic tools may be incorporated through the cutter or similar openings.

For another example, although a localization mechanism 16 is depicted that laterally compresses a downward hanging patient's breast, aspects of the present invention are applicable to other orientations of localization and imaging.

As an additional example, although MRI is discussed herein as the imaging modality for stereotopically guiding the core biopsy, aspects of the present invention apply to other imaging modalities.

As yet a further example, although a Cartesian X-Y-Z positioning approach is disclosed herein, it will be appreciated that a polar or spherical positioning approach may be implemented in whole or in part so that the detachable probe assembly enters at a predefined angle.

As yet an additional example, although a prone breast compression device is depicted, application of the present invention may be used in medical compression devices oriented in other manners, to include standing, lying on one side, or supine. In addition, aspects of the present invention may be applicable to positioning a biopsy probe through a medial compression plate, or a top and bottom compression plate pair, instead of a lateral compression plate. Furthermore, aspects of the present invention are applicable to other diagnostic imaging modalities currently used or that become available in the future. In addition, aspects of the present invention would have application to diagnostic guided biopsy procedures on other portions of the body, as well as to positioning a probe for utilizing other diagnostic and treatment devices in a minimally invasive manner.

As yet a further example, an elongate needle may be formed without a structural, longitudinal barrier between the vacuum chamber lumen and the cutter lumen. Instead, the advancing cutter 90 may define a cutter lumen having a circular cross section within a noncircular cross section (e.g., oval) of the internal cavity of the elongate needle. Moreover, a noncircular liner may be used to prevent adhesive entering the undifferentiated internal cavity.

What is claimed is:

1. A method of performing a biopsy of tissue located at coordinates in a first, second, and third dimension, the method comprising:
(a) localizing a patient's breast in a localization fixture, wherein the localization fixture comprises:
(i) a probe assembly comprising:
a proximal end, a distal end, a lumen, an opening in communication with the lumen, wherein the opening is positioned proximate to the distal end, and an insertion tool operable to selectively block the opening, (ii) a probe assembly guide coupled to the probe assembly, and (iii) a compression plate operable to stabilize the patient's breast, wherein the compression plate comprises:

elongate slots extending along the first dimension, wherein the slots are spaced apart along the second dimension, wherein the act of localizing the patient's breast comprises compressing at least a portion of the breast with the compression plate;

(b) locating suspicious tissue with an MRI scan;

(c) defining coordinates in the first, second, and third dimensions that correspond to the location of the suspicious tissue;

(d) inserting the probe assembly into the patient's breast guided by the probe assembly guide, wherein the probe assembly is inserted along the third dimension, wherein the probe assembly is inserted through one of the elongate slots of the compression plate;

(e) performing a selected one of a diagnostic procedure, surgical procedure and a therapeutic procedure with the probe assembly inserted into tissue and detached from a biopsy instrument;

(e) engaging a handle of the biopsy instrument to the proximal end of the probe assembly, wherein the biopsy instrument comprises a cutter sized to translate in the lumen of the probe assembly, wherein the cutter is retracted in the handle at the initiation of the act of coupling the handle to the probe assembly; and (f) advancing the cutter through the lumen in the probe assembly to the tissue.

2. The method of claim 1, wherein the probe assembly further comprises a needle, wherein the opening of the probe assembly comprises a cutter opening laterally presented near the distal end of the probe assembly, the probe assembly further comprising a vacuum lumen and a cutter lumen, wherein the cutter lumen is configured to receive the cutter of the biopsy instrument, wherein the vacuum lumen and cutter lumen are both in fluid communication between the proximal end of the probe assembly and the cutter opening of the probe assembly, the method further comprising:

with the biopsy instrument engaged to the probe assembly, applying vacuum through the biopsy instrument and through the lumens of the probe assembly.

3. The method of claim 2, further comprising:

sealing the cutter lumen with an obturator stylet that allows fluid communication between the vacuum lumen and the cutter opening.

4. The method of claim 1, wherein performing the selected one of the diagnostic procedure, surgical procedure and the therapeutic procedure with the probe assembly inserted into tissue and detached from a biopsy instrument further comprises with the biopsy instrument disengaged from the probe assembly, transferring fluid through the inserted probe assembly for a therapeutic treatment.

5. The method of claim 1, wherein performing the selected one of the diagnostic procedure, surgical procedure and the therapeutic procedure with the probe assembly inserted into tissue and detached from a biopsy instrument further comprises inserting a tool through the proximal end of the probe assembly.

6. The method of claim 1, wherein the probe assembly includes a target operable to present an artifact to an MRL machine, the method further comprising:

with the probe assembly inserted into the tissue and the biopsy instrument disengaged, positioning the patient within a closed MRI machine bore and performing an MRI scan.

7. The method of claim 1, further comprising:

coupling a fiducial marker to the localization fixture.

8. The method of claim 1, further comprising:

attaching a tip protector onto the probe assembly, the tip protector including a fiducial marker;

attaching the probe assembly to the probe assembly guide; and positioning the probe assembly guide for a desired spatial coordinate.

9. The method of claim 1, further comprising:

locating the probe assembly guide to a desired insertion point on the localization fixture; and using the probe assembly guide to insert the probe to a desired biopsy site at a constrained angle.

10. The method of claim 1, wherein performing the selected one of the diagnostic procedure, surgical procedure and a therapeutic procedure with the probe assembly inserted into tissue and detached from a biopsy instrument comprises imaging the probe assembly to confirm a location of an area of interest in the tissue relative to the inserted probe assembly.

11. A method of a diagnostic imaging guided minimally invasive procedure, comprising:

(a) localizing a human breast in a localization fixture;

(b) stabilizing the human breast using a compression plate including a series of apertures, wherein the act of stabilizing comprises compressing at least a portion of the breast with the compression plate;

(c) diagnostic imaging the human breast to locate a tissue location;

(d) attaching a probe assembly to a probe guide assembly coupled to the localization fixture;

(e) positioning the probe guide assembly to a lateral spatial location on the human breast;

(f) guiding the probe guide assembly along horizontal and vertical directions parallel to the lateral spatial location on the human breast to an insertion angle to position the probe assembly at the tissue location;

(g) inserting the probe assembly into the human breast guided by the probe guide assembly toward a medial side of the human breast, wherein the act of inserting the probe assembly further comprises inserting the probe assembly through one of the apertures of the compression plate;

(h) engaging a handle including a cutter to the probe assembly to obtain a core biopsy sample through the probe assembly, wherein the cutter is fully retracted within the handle when the handle is initially engaged to the probe assembly, such that the cutter does not protrude from the handle when the handle is initially engaged to the probe assembly; and (i) advancing the cutter relative to the handle and into the probe assembly to sever a tissue sample.

12. The method of claim 11, wherein guiding the probe assembly along the insertion angle further comprises:

using a depth adjustment mechanism to gain mechanical advantage.

13. The method of claim 11, wherein guiding the probe assembly along the insertion angle further comprises referring to depth position indicia.

14. The method of claim 11, wherein positioning the probe assembly to a spatial location on the body portion further comprises:

adjusting the probe guide assembly to a desired horizontal position; and adjusting the probe guide assembly to a desired vertical position.

15. The method of claim 14 wherein adjusting the probe guide assembly to a desired horizontal and vertical position further comprises referring to horizontal and vertical position indicia.

16. The method of claim 11, wherein the probe assembly includes a cutter lumen and a vacuum lumen in fluid communication with the cutter lumen, and wherein the act of advancing the cutter further comprises:

inserting the cutter through the cutter lumen for severing a tissue sample; and drawing a vacuum through the vacuum lumen to assist in drawing in the tissue sample into the cutter lumen.

17. The method of claim 16, further comprising:

transferring a fluid through the vacuum lumen to perform a therapeutic treatment to the tissue location.

18. A method for performing a biopsy, the method comprising:

(a) localizing a body portion in a localization fixture, wherein the localization fixture comprises:

(i) a probe assembly comprising:
 a proximal end,
 a distal end,
 a cutter lumen, and
 an opening in communication with the cutter lumen, wherein the opening is positioned proximate to the distal end, (ii) a probe assembly guide coupled to the probe assembly, and (iii) a compression plate operable to stabilize the body portion, wherein the compression plate comprises apertures arranged along first and second dimensions, wherein the act of localizing comprises compressing at least a portion of the body portion with the compression plate;

(b) imaging the body portion to determine a tissue location relative to the localization fixture;

(c) determining the tissue location relative to the localization fixture with respect to first, second, and third dimensions;

(d) positioning the probe assembly at the tissue location relative to the first and second dimensions guided by the probe assembly guide;

(e) inserting the probe assembly along the third dimension to place the opening of the probe assembly proximate to the tissue location, wherein the act of inserting comprises inserting the probe assembly through one of the apertures of the compression plate;

(f) imaging the body portion to determine the tissue location relative to the inserted probe assembly;

(g) coupling a handle of a biopsy instrument to the probe assembly, wherein the biopsy instrument comprises a cutter configured to translate through the cutter lumen of the probe assembly, wherein the biopsy instrument is configured to selectively engage with the probe assembly, wherein the cutter is retracted within the handle at the initiation of the act of coupling the handle to the probe assembly;

(h) advancing the cutter of the biopsy instrument through the cutter lumen of the probe assembly; and (i) severing a portion of tissue at the tissue location with the cutter, wherein the portion of tissue is severed adjacent the opening of the probe assembly.

19. The method of claim 18, wherein the opening of the probe assembly is blocked during the act of inserting the probe assembly into the body portion, the method further comprising unblocking the opening of the probe assembly prior to advancing the cutter of the biopsy instrument.

20. The method of claim 18, the method further comprising substantially restraining movement of the probe assembly guide along the first and second dimensions after the act of positioning the probe guide assembly at the tissue location relative to the first and second dimensions.

21. The method of claim 18, the method further comprising substantially restraining movement of the probe assembly along the third dimension after the act of inserting the probe assembly into the body portion.

22. The method of claim 18, wherein the biopsy instrument comprises a drive mechanism operable to communicate linear and rotational movement to the cutter, wherein the act of advancing the cutter comprises communicating linear movement to the cutter with the drive mechanism, and wherein the act of severing a portion of tissue comprises communicating rotational movement to the cutter with the drive mechanism.

23. The method of claim 18, wherein the biopsy instrument further comprises a window, wherein the window is located proximate to the proximal end of the probe assembly when the biopsy instrument is coupled to the probe assembly, wherein the method further comprises extracting the severed portion of tissue through the window.

* * * * *